US012115002B2

(12) United States Patent
Antonio et al.

(10) Patent No.: US 12,115,002 B2
(45) Date of Patent: *Oct. 15, 2024

(54) ANALYTE SENSOR

(71) Applicant: MEDTRONIC MINIMED, INC., Northridge, CA (US)

(72) Inventors: David C. Antonio, Pasadena, CA (US); Eric Allan Larson, Simi Valley, CA (US); Jose J. Ruelas, San Fernando, CA (US); Sukhjeet S. Ranauta, Canoga Park, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 538 days.

This patent is subject to a terminal disclaimer.

(21) Appl. No.: 16/943,677

(22) Filed: Jul. 30, 2020

(65) Prior Publication Data

US 2020/0359964 A1    Nov. 19, 2020

Related U.S. Application Data

(60) Division of application No. 15/478,110, filed on Apr. 3, 2017, now Pat. No. 10,765,369, which is a
(Continued)

(51) Int. Cl.
*A61B 5/00* (2006.01)
*A61B 5/145* (2006.01)
(Continued)

(52) U.S. Cl.
CPC ........ *A61B 5/6849* (2013.01); *A61B 5/14503* (2013.01); *A61B 5/14532* (2013.01);
(Continued)

(58) Field of Classification Search
CPC ............ A61B 5/14503; A61B 5/14532; A61B 5/1473; A61B 5/14865; A61B 5/6833;
(Continued)

(56) References Cited

U.S. PATENT DOCUMENTS 4,562,751 A    1/1986   Nason et al.
4,573,994 A    3/1986   Fischell et al.
(Continued)

FOREIGN PATENT DOCUMENTS

CA       3022146 C      4/2023
CN       102469967 A    5/2012
(Continued)

*Primary Examiner* — Puya Agahi
(74) *Attorney, Agent, or Firm* — Fortem IP LLP

(57) ABSTRACT

A simple, disposable sensing device for sensing an analyte is housed in a single case. The sensing device can transmit sensor data to monitoring device(s). The sensing device includes: a case having a lower major wall adapted to be mounted against a patient's skin, and an upper opposing major wall; a sensor extending from the case and having a distal end sensitive to the analyte to produce an electrical signal, and a proximal end within the case having electrical contacts; a printed circuit board assembly within the case supported by one of the major walls to receive the electrical signal via the electrical contacts; and an elastomeric pad disposed in the case and biased by the other major wall to urge the proximal end of the sensor into contact with the printed circuit board assembly and maintain an electrical connection between the electrical contacts and the printed circuit board assembly.

13 Claims, 27 Drawing Sheets

Related U.S. Application Data continuation-in-part of application No. 15/357,885, filed on Nov. 21, 2016, now Pat. No. 10,631,787, and a continuation-in-part of application No. 15/357,925, filed on Nov. 21, 2016, now Pat. No. 10,420,508, and a continuation-in-part of application No. 15/357,952, filed on Nov. 21, 2016, now Pat. No. 10,413,183.

(60) Provisional application No. 62/320,290, filed on Apr. 8, 2016, provisional application No. 62/344,847, filed on Jun. 2, 2016, provisional application No. 62/344,852, filed on Jun. 2, 2016, provisional application No. 62/402,676, filed on Sep. 30, 2016, provisional application No. 62/460,710, filed on Feb. 17, 2017.

(51) Int. Cl.
*A61B 5/1473* (2006.01)
*A61B 5/1486* (2006.01)
*A61B 17/34* (2006.01)

(52) U.S. Cl.
CPC ........ *A61B 5/1473* (2013.01); *A61B 5/14865* (2013.01); *A61B 5/6833* (2013.01); *A61B 5/742* (2013.01); *A61B 5/746* (2013.01); *A61B 17/3468* (2013.01); *A61B 2560/0219* (2013.01); *A61B 2560/0406* (2013.01); *A61B 2560/0412* (2013.01); *A61B 2560/045* (2013.01); *A61B 2560/0468* (2013.01); *A61B 2560/063* (2013.01); *A61B 2562/125* (2013.01); *A61B 2562/166* (2013.01); *A61B 2562/227* (2013.01)

(58) Field of Classification Search
CPC ..... A61B 5/742; A61B 5/746; A61B 17/3468; A61B 2562/227
See application file for complete search history.

(56) References Cited

U.S. PATENT DOCUMENTS

| | | |
|---|---|---|
| 4,678,408 A | 7/1987 | Nason et al. |
| 4,685,903 A | 8/1987 | Cable et al. |
| 4,755,173 A | 7/1988 | Konopka et al. |
| 5,299,571 A | 4/1994 | Mastrototaro |
| 5,390,671 A | 2/1995 | Lord et al. |
| 5,391,250 A | 2/1995 | Cheney, II et al. |
| 5,482,473 A | 1/1996 | Lord et al. |
| 5,485,408 A | 1/1996 | Blomquist |
| 5,522,803 A | 6/1996 | Teissen-Simony |
| 5,568,806 A | 10/1996 | Cheney, II et al. |
| 5,586,553 A | 12/1996 | Halili et al. |
| 5,665,065 A | 9/1997 | Colman et al. |
| 5,800,420 A | 9/1998 | Gross et al. |
| 5,807,375 A | 9/1998 | Gross et al. |
| 5,851,197 A | 12/1998 | Marano et al. |
| 5,925,021 A | 7/1999 | Castellano et al. |
| 5,954,643 A | 9/1999 | Van Antwerp et al. |
| 6,011,984 A | 1/2000 | Van Antwerp et al. |
| 6,017,328 A | 1/2000 | Fischell et al. |
| 6,093,172 A | 7/2000 | Funderburk et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,293,925 B1 * | 9/2001 | Safabash ............... A61M 5/158 604/157 |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,228,159 B2 | 6/2007 | Petersson et al. |
| 7,303,549 B2 | 12/2007 | Flaherty et al. |
| 7,399,277 B2 | 7/2008 | Saidara et al. |
| 7,442,186 B2 | 10/2008 | Blomquist |
| 7,574,262 B2 | 8/2009 | Haugland et al. |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,751,863 B2 | 7/2010 | Markle et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,467,843 B2 | 6/2013 | Markle et al. |
| 9,399,076 B2 | 7/2016 | Yu et al. |
| 2006/0036145 A1 * | 2/2006 | Brister ................. A61B 5/6849 600/345 |
| 2007/0123819 A1 | 5/2007 | Mernoe et al. |
| 2007/0241126 A1 | 10/2007 | Micinski |
| 2008/0125636 A1 | 5/2008 | Ward et al. |
| 2009/0105569 A1 | 4/2009 | Stafford |
| 2009/0124979 A1 | 5/2009 | Lopez et al. |
| 2009/0326355 A1 | 12/2009 | Brenneman et al. |
| 2010/0160861 A1 | 6/2010 | Causey, III et al. |
| 2010/0198034 A1 | 8/2010 | Thomas et al. |
| 2010/0286607 A1 | 11/2010 | Saltzstein |
| 2011/0060196 A1 | 3/2011 | Stafford |
| 2011/0319729 A1 | 12/2011 | Donnay et al. |
| 2012/0238851 A1 | 9/2012 | Kamen et al. |

(56) References Cited

U.S. PATENT DOCUMENTS

| | | |
|---|---|---|
| 2012/0265042 A1 | 10/2012 | Neinast et al. |
| 2013/0150691 A1 | 6/2013 | Pace et al. |
| 2013/0267811 A1 | 10/2013 | Pryor et al. |
| 2013/0267813 A1 | 10/2013 | Pryor et al. |
| 2013/0292354 A1 | 11/2013 | Xu et al. |
| 2013/0313130 A1 | 11/2013 | Little et al. |
| 2015/0164390 A1 | 6/2015 | Larvenz et al. |
| 2015/0190075 A1* | 7/2015 | Stafford ............... A61B 5/1451 29/407.1 |
| 2015/0216501 A1 | 8/2015 | Mailaender et al. |
| 2016/0015303 A1 | 1/2016 | Bernstein et al. |
| 2016/0058380 A1 | 3/2016 | Lee et al. |
| 2017/0030889 A1 | 2/2017 | Yao et al. |
| 2017/0112534 A1 | 4/2017 | Schoonmaker et al. |
| 2017/0188910 A1 | 7/2017 | Halac et al. |
| 2020/0214633 A1 | 7/2020 | Antonio et al. |
| 2020/0352485 A1 | 11/2020 | Antonio et al. |
| 2024/0252114 A1 | 8/2024 | Antonio et al. |

FOREIGN PATENT DOCUMENTS

| | | |
|---|---|---|
| CN | 103991629 A | 8/2014 |
| EP | 1752944 A2 | 2/2007 |
| EP | 2701600 | 3/2014 |
| EP | 2701600 B1 | 6/2016 |
| WO | 9610442 A1 | 4/1996 |
| WO | 0035530 A1 | 6/2000 |
| WO | 2006094513 A2 | 9/2006 |
| WO | 2011001916 A1 | 1/2011 |
| WO | 2011041531 A1 | 4/2011 |
| WO | 2012149143 A1 | 11/2012 |
| WO | 2017176797 A1 | 10/2017 |

\* cited by examiner

ANALYTE SENSOR

CROSS-REFERENCE TO RELATED APPLICATIONS

This application is a divisional of U.S. patent application Ser. No. 15/478,110, filed on Apr. 3, 2017, which is: a continuation-in-part of U.S. patent application Ser. No. 15/357,885, filed on Nov. 21, 2016 (issued on Apr. 28, 2020 as U.S. Pat. No. 10,631,787); a continuation-in-part of U.S. patent application Ser. No. 15/357,925, filed on Nov. 21, 2016 (issued on Sep. 24, 2019 as U.S. Pat. No. 10,420,508); and a continuation-in-part of U.S. patent application Ser. No. 15/357,952, filed on Nov. 21, 2016 (issued on Sep. 17, 2019 as U.S. Pat. No. 10,413,183). U.S. patent application Ser. No. 15/478,110 claims priority to, and the benefit of: U.S. Provisional Patent Application Ser. No. 62/320,290 filed on Apr. 8, 2016; U.S. Provisional Application Ser. No. 62/344,847 filed on Jun. 2, 2016; U.S. Provisional Patent Application Ser. No. 62/344,852 filed on Jun. 2, 2016; U.S. Provisional Patent Application Ser. No. 62/402,676 filed on Sep. 30, 2016; and U.S. Provisional Patent Application Ser. No. 62/460,710 filed on Feb. 17, 2017. The contents of the applications listed above are incorporated herein by reference in their entirety.

BACKGROUND OF THE DISCLOSURE

Field of the Disclosure

The present disclosure generally relates to a sensor for monitoring a body characteristic of the body, such as glucose. More particularly, the present disclosure relates to a single device including a sensor, transmitter and inserter. The present disclosure further relates to a simple to use continuous glucose monitoring device with visual indicators.

Description of the Related Art

In recent years, a variety of electrochemical sensors have been developed for a range of applications, including medical applications for detecting and/or quantifying specific agents in a patient's blood and other body fluids. As one example, glucose sensors have been developed for use in obtaining an indication of blood glucose levels in a diabetic patient. Such readings can be especially useful in monitoring and/or adjusting a treatment regimen which typically includes regular administration of insulin to the patient. In this regard, blood glucose readings are particularly useful in conjunction with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994.

It is often difficult to get pre- and type 2 diabetic patients to embrace monitoring of their blood sugar on a regular basis. However, it is very important for their health that they learn how to be careful about their blood glucose levels and know how to adjust their diets and other medicines. Thus, there is a strong need for more efficient, more comfortable, and even simpler blood glucose monitors.

Relatively small and flexible electrochemical sensors have been developed for subcutaneous placement of sensor electrodes in direct contact with patient blood or other extracellular fluid, wherein such sensors can be used to obtain periodic readings over an extended period of time. In one form, flexible transcutaneous sensors are constructed in accordance with thin film mask techniques wherein an elongated sensor includes thin film conductive elements encased between flexible insulative layers of polyimide sheet or similar material. Such thin film sensors typically include exposed electrodes at a distal end for subcutaneous placement in direct contact with patient blood or the like, and exposed conductive contact pads at an externally located proximal end for convenient electrical connection with a suitable monitoring device. Such thin film sensors hold significant promise in patient monitoring applications, but unfortunately have been difficult to place transcutaneously with the sensor electrodes in direct contact with patient blood or other body fluid. Improved thin film sensors and related insertion sets are described in commonly assigned U.S. Pat. Nos. 5,390,671; 5,391,250; 5,482,473; 5,299,571; 5,586,553, 5,568,806, and 7,602,310 which are incorporated by reference herein.

Currently, glucose sensor sets exist that include three components: a disposable sensor with its mounting base, a durable, rechargeable transmitting device, and a durable sensor insertion tool. Because it is necessary to regularly replace the sensors sold with or to be used with these sets, these sets present some challenges to the user. The user must pause any continuous glucose monitoring to recharge the transmitting device during sensor replacement. The insertion process is often long and complex. After insertion, the transmitting device must be connected to the sensor, often on hard to reach insertion sites. After connecting the transmitter, it is common for a user to have to wait over an hour before the sensor starts giving readings, resulting in a break of the monitoring process. During the break, blood glucose spikes will be unrecognized by the monitoring device.

Currently, there are sensor sets that include a mounting base, for placement on the patient's skin, which can be coupled to a connector with suitable sensor electronics (wired or wireless). Because the mounting base may be sold separately, it is possible to attach incompatible components together, which can compromise the sensor data. In addition, the structure of the current sensors allows for limited number of contact pads, and respective sensor electrodes.

SUMMARY OF THE DISCLOSURE

In aspects, provided herein is a sensing device for sensing a patient characteristic like an analyte (e.g., glucose), the device comprising: a single case adapted to be mounted on the skin of the patient; a printed circuit board assembly inside the case; a first sensor extending from the case, the first sensor having at least two sensor electrodes thereon at a distal end for generating at least one electrical signal representative of an analyte, the first sensor including at least two contact pads at a proximal end, wherein the at least two contact pads are electrically coupled to the printed circuit board assembly, wherein each of the at least two contact pads are electrically coupled to at least one of the at least two sensor electrodes, and wherein the distal end of the first sensor extends from the case; a transmitter electrically coupled to the printed circuit board assembly and inside the case, wherein the transmitter is adapted to transmit signals sensed by the sensor; a battery electrically coupled to the printed circuit board assembly and inside the case.

Also provided is a method of sensing an analyte, comprising providing the sensing device, inserting the sensor into the body of a patient using an insertion tool, wherein the insertion tool is adapted to hold the case inside the insertion tool and wherein the insertion tool includes a needle adapted to surround the sensor and to pierce the body of the patient, removing the insertion tool such that the sensing device remains on the body of the patient with the sensor inside the body of the patient.

The proximal end of the sensor may be permanently affixed to the printed circuit board assembly. The printed circuit board assembly may include printed circuit board assembly sensor pads, the printed circuit board assembly sensor pads adapted to electrically couple to the first sensor contact pads, and further include a sensor elastomeric connector on top of the first sensor and the printed circuit board assembly, wherein the sensor elastomeric connector presses the first sensor contact pads directly against the printed circuit board assembly sensor pads.

A second sensor may be included, the second sensor having at least two sensor electrodes thereon at a distal end for generating at least one electrical signal representative of the analyte, the second sensor including at least two contact pads at a proximal end, wherein the at least two contact pads are electrically coupled to the printed circuit board assembly, wherein each of the at least two contact pads are electrically coupled to at least one of the at least two sensor electrodes, and wherein the distal end of the second sensor extends from the case. The proximal end of the second sensor may be stacked on the proximal end of the first sensor, wherein the at least two contact pads on the first sensor face in the opposite direction of the at least two contact pads on the second sensor. The at least two sensor electrodes on the distal end of the first sensor may also be formed in the opposite direction as the at least two sensor electrodes on the distal end of the second sensor.

The sensing device may include a battery pull tab adapted to break the electrical coupling of the battery from the printed circuit board assembly. The printed circuit board assembly may include battery connector pads that must be shorted together to connect the positive side of the battery to the printed circuit board assembly, and further include a pull tab elastomeric connector adapted to short the battery connector pads when it contacts the printed circuit board assembly. The battery pull tab is adapted to separate the battery connector pads from the pull tab elastomeric connector when it is located between the battery connector pads and the pull tab elastomeric connector. The sensing device may further include a battery pull tab retaining post on the printed circuit board assembly, wherein the battery pull tab is affixed to the battery pull tab retaining post. The battery pull tab may include a tear notch adapted to tear the battery pull tab from the battery pull tab retaining post such that the battery pull tab is removed from the sensing device, whereby the pull tab elastomeric connector contacts the battery connector pads. There may be more than one battery, such as two batteries connected in series.

The sensing device is housed in a single housing or case. The case may comprise an upper housing and a lower housing. The upper housing is connected to the lower housing in a water tight manner. For example, the upper housing may be ultrasonically welded to the lower housing. In an embodiment, the sensing device is smaller than multiple part sensing devices of the prior art. For example, the sensing device may be less than about 1.4 inches by 1 inch by 0.2 inches in size.

The transmitter transmits the sensor signals to a monitoring device, such as a handheld analyte monitor, which may have a display, or a smartphone.

The sensing device may include a push button or other type of switch instead of a pull tab for powering on the device. Instead of being completely disconnected during storage, the battery may be connected with the sensing device in a low power sleep mode.

In aspects, herein is provided a sensing device for self-monitoring an analyte, the sensing device including a flexible case adapted to adhere to the skin of a patient, a printed circuit board assembly inside the case, a first sensor extending from the flexible case and electrically coupled to the printed circuit board, and one or more indicators such as lights in the flexible case, where the indicator(s) are adapted to indicate whether a level of analyte is within a normal range. The sensing device may in addition or alternatively show the percentage of time a level of analyte has been within a desired range.

The sensing device for self-monitoring an analyte may also keep track of the percentage of a predetermined amount of time that the level of the analyte is within the normal range. The predetermined amount of time may be set as 24 hours, or it may be set as 7 days.

In some aspects, one or more indicators may be adapted to indicate the percentage of the predetermined amount of time that the level of analyte was within the normal range. The one or more indicators may include a light adapted to turn on when the analyte level was within the normal range for greater than ninety percent of the predetermined amount of time.

In some aspects, the one or more indicators are LED lights. The one or more indicators may each be capable of displaying at least two colors. In aspects, the one or more indicators are configured to blink, such that quick blinking indicates higher than normal levels of the analyte and slow blinking indicates lower than normal levels of the analyte. In some aspects, the one or more indicators includes a light adapted to display a first color when the level of the analyte is normal and adapted to display a second color when the level of the analyte is outside of a normal range. In some aspects, numerous indicators can make up a shape of lights to indicate a sliding scale of the level of the analyte.

The sensing device for self-monitoring an analyte may be a disposable, one-time use device. In some aspects, the sensing device may include an adhesive patch adapted to attach the flexible case to the skin of the patient.

In an aspect, the sensor is a microneedle sensor. In some aspects, the sensor may be a flexible thin film sensor adapted to be inserted in the skin of a patient using an insertion needle. The analyte may be blood glucose.

In some aspects, the sensing device for self-monitoring an analyte may include a single use, disposable battery. It may also include a pull tab adapted to prevent the sensor device from turning on until it is removed from the sensing device.

In some aspects, the sensor of the sensing device may include at least two sensor electrodes thereon at a distal end for generating at least one electrical signal representative of an analyte, the first sensor including at least two contact pads at a proximal end, wherein the at least two contact pads are electrically coupled to the printed circuit board assembly, wherein each of the at least two contact pads are electrically coupled to at least one of the at least two sensor electrodes, and wherein the distal end of the first sensor extends from the case. In some aspects, the sensing device may include a second sensor, the second sensor having at least two sensor electrodes thereon at a distal end for generating at least one electrical signal representative of the analyte, the second sensor including at least two contact pads at a proximal end, wherein the at least two contact pads are electrically coupled to the printed circuit board assembly, wherein each of the at least two contact pads are electrically coupled to at least one of the at least two sensor electrodes, and wherein the distal end of the second sensor extends from the case.

In aspects, herein is provided a medical sensing device for sensing an analyte, the device comprising a case having a lower major wall adapted to be mounted against the skin of the patient, and an upper opposing major wall; a sensor extending from the case and having a distal end sensitive to the analyte to produce an electrical signal, and a proximal end within the case having electrical contacts; a printed circuit board assembly within the case supported by one of the major walls to receive the electrical signal via the electrical contacts; and an elastomeric pad disposed in the case and biased by the other major wall to urge the said proximal end of the sensor into contact with the printed circuit board assembly and maintain an electrical connection between the electrical contacts and the printed circuit board assembly.

The electrical contacts on the sensor may face the contact pads on the printed circuit board assembly; and the elastomeric pad presses the electrical contacts on the sensor into touching connection with corresponding contact pads on the printed circuit board assembly to maintain the electrical connection. The electrical contacts on the sensor may face away from the printed circuit board assembly; the printed circuit board assembly has contact pads displaced to the side of the sensor, and the elastomeric pad contains conductive strips positioned to connect electrically the contact pads of the printed circuit board assembly to respective electrical contacts of the sensor to maintain the electrical connection.

The proximal end of the sensor may have electrical contacts facing both towards and away from the printed circuit board assembly; the printed circuit board assembly has first contact pads touching the contacts facing towards the printed circuit board assembly, and second contact pads displaced to the side of the sensor; the elastomeric pad being disposed to press the electrical contacts on the sensor facing the printed circuit board assembly into touching connection with first contact pads; the elastomeric pad further containing conductive strips positioned to connect electrically the second contact pads of the printed circuit board assembly to respective electrical contacts of the sensor facing away from the printed circuit board assembly. The elastomeric pad may have alternating conductive layers and non-conductive layers along its length such that the elastomeric pad is conductive along its width and height, but not along its length.

The sensor may comprise two strips of insulative sheet material each having on its surface elongate conductive elements leading from the distal end to the contacts at the proximal end, wherein the strips are arranged back-to-back such that the contacts on one strip face towards the printed circuit board assembly and the contacts on the other strip face away from the printed circuit board assembly. The sensor may extend from the case via an opening in the lower major wall, there being a seal separating the opening from an internal cavity of the case housing of the printed circuit board assembly, said seal being held in compression between the upper and lower walls, wherein the back-to-back strips separate to a side-by-side relationship where they pass through the seal.

The sensing device may further include a transmitter electrically coupled to the printed circuit board assembly and inside the case, wherein the transmitter is adapted to transmit analyte readings sensed by the sensor. The sensing device may further include a battery electrically coupled to the printed circuit board assembly and inside the case. The sensing device may further include a battery pull tab adapted to break the electrical coupling of the battery from the printed circuit board assembly. The sensing device may further include battery connector pads that must be shorted together to connect the battery to the printed circuit board assembly, a pull tab elastomeric connector biased in a direction to short the battery connector pads, wherein the battery pull tab is adapted to separate the battery connector pads from the pull tab elastomeric connector until it is pulled. The battery connector pads may be on the printed circuit board assembly, which further may have a battery pull tab retaining post, wherein the battery pull tab is affixed to the battery pull tab retaining post. The sensing device may include a button in the upper major wall, wherein the button is adapted to activate the sensing device.

The case may comprise an upper housing including the upper major wall and a lower housing including the upper major wall, and wherein the upper housing is connected to the lower housing in a water tight manner. The upper housing may be ultrasonically welded to the lower housing. The case may be less than about 1.4 inches by 1 inch by 0.2 inches in size.

In aspects, provided herein is a medical sensing device for sensing an analyte, the device comprising: a case having a lower major wall adapted to be mounted against the skin of the patient, and an upper opposing major wall; a sensor extending from the case through an opening in the lower major wall, the sensor and having a distal end sensitive to the analyte to produce an electrical signal, and a proximal end within the case having electrical contacts; a power unit disposed at a first end of the case; a T-shaped support mounted within the case having a cross arm extending transversely across the case, and a stem extending towards a second end of the case, the stem having a guide channel for the sensor from the opening in the lower major wall.

The T-shaped support has support pads at the ends of the cross arm in contact with the upper major wall. The upper major wall may have an orifice for entry of a needle, and the support may extend to the upper major wall at the intersection of the cross arm and stem and provides a guide for the needle. The lower major wall may comprise a printed circuit board assembly supporting the power unit and the T-shaped support, the printed circuit board assembly further having pads connecting to the electrical contacts of the sensor. The casing may be made of a flexible material, for example and without limitation, silicone or polyurethane.

According to a further aspect the disclosure provides apparatus for placing a medical device on the surface of the skin of a patient and inserting a medical filament extending from the device into the skin of the patient. Typically, but not necessarily the medical device can contain the electronics of a glucose sensor and a transmitter to transmit measured readings to external equipment. In that case the filament could be the electrodes of a potentiostat and connecting wires. The apparatus comprises a frame having a mouth for positioning against the skin during placement of the medical device, and an internal cavity for retention of the medical device prior to placement. Typically the apparatus comes pre-assembled with a pull off cover over the mouth preventing premature actuation. The medical device itself has a surface adapted to be held against the skin of the patient and the filament extends therefrom. Most conveniently the said surface could be provided with an adhesive layer, or be attached to an adhesive patch. The apparatus further has a retractable needle extending through the medical device and carrying the filament. The needle typically has an internal longitudinal cavity or "C" cross section so that it protects and carries the filament during insertion. When the needle is retracted it leaves the filament implanted. The apparatus has a striker holding the medical device and being axially movable within the frame from a first retracted position within the frame to a second position in which the surface of the medical device is presented at the mouth of the frame. When in position on the skin of the patient, any adhesive on the medical device could at this stage stick to the skin. The apparatus further includes a driver, for example a coil spring configured to urge the striker towards the second position and a releasable striker lock holding the striker in the first position. The apparatus has a plunger axially movable with respect to the frame in a direction towards the mouth, from a rest position to a firing position, the apparatus having a mechanism configured to release the striker lock when the plunger reaches the firing position, allowing the striker to move from the retracted to the second position. The driver spring may be longitudinally disposed between the striker and the plunger, such as to compress as the plunger is moved from the rest position to the firing position. The striker lock may comprise an engagement between upstanding extensions on the frame and the striker, and the plunger may have a cam surface to dislodge the engagement. Thus in this arrangement when the patient holds the plunger and presses the apparatus against the skin, this does not directly press the striker, and hence the needle into the skin, but compresses the spring. As manual pressure is exerted on the plunger compressing the spring this creates a corresponding force on the patient, which helps stabilize the apparatus. This reaction force is supplemented by the reaction to the force needed to release this lock, thus improving stability even more, especially at the firing time.

The striker may have resilient snap arms engaging a perimeter of the medical device to releasably hold the medical device in the striker. The releasability of the medical device enables the apparatus to be lifted off the skin leaving the medical device in place. To help prevent premature release of the medical device, the frame has ribs, which contact the arms when the striker is in the first position. This increases the force needed to release the medical device from the striker, before the firing. The ribs may be fixed on the frame and extend longitudinally into the striker, touching the snap arms only when the striker is in the first position, increasing their stiffness and or flexing length. The medical device may be rectangular, possibly with rounded corners and be held in the striker by four of said snap arms, one acting on each corner.

The apparatus may further include an automatic retractor exerting a force on the needle in the direction to pull the needle out of the medical device; a releasable retractor lock preventing the retractor from pulling the needle out of the medical device; and a retractor lock release mechanism configured to release when the striker is in the second position and the plunger moves away from the firing position. The retractor may be spring acting on a needle hub attached to the proximal end of the needle.

The plunger may comprise a push button head adapted to be gripped by the user merging via a shoulder portion to a wider diameter dependent skirt portion; and the apparatus may further include an external collar surrounding the frame and spaced therefrom to form an annular gap accommodating the dependent skirt of the plunger. The collar may be rotatable with respect to the plunger and there may be provided locking structures allowing axial movement of the plunger with respect to the frame at a given angular orientation. The locking structures may include a visible indication of the angular orientation at which the plunger can be axially moved.

The disclosure according to a modification of this aspect also envisages the arrangements to vary the holding force with which the medical device is held in a simplified context too. The disclosure thus also provides apparatus for placing a medical device on the surface of the skin of a patient and inserting a medical filament extending from the device into the skin of the patient, comprising a frame having a mouth for positioning against the skin during placement of the medical device, and an internal cavity for retention of the medical device prior to placement; the medical device having a surface adapted to be held against the skin of the patient and having the filament extending therefrom; a retractable needle extending through the medical device and carrying the filament; a striker holding the medical device and being axially movable within the frame from a first retracted position within the frame to a second position in which the surface of the medical device is presented at the mouth of the frame; a plunger being axially movable with respect to the frame in a direction towards the mouth; wherein the striker has resilient snap arms engaging a perimeter of the medical device to releasably hold the medical device in the striker; and the frame has ribs which contact the arms when the striker is in the first position to increase the force needed to release the medical device from the striker.

In aspects, an apparatus for placing a medical device on the surface of the skin of a patient and inserting a medical filament extending from the device into the skin of the patient is provided, the apparatus comprising: a frame having a mouth for positioning against the skin during placement of the medical device, and an internal cavity for retention of the medical device prior to placement; the medical device having a surface adapted to be held against the skin of the patient and having the filament extending therefrom; a retractable needle extending through the medical device and carrying the filament; a striker holding the medical device and being axially movable within the frame from a first retracted position within the frame to a second position in which the surface of the medical device is presented at the mouth of the frame; a driver configured to urge the striker towards the second position; a releasable striker lock holding the striker in the first position; a plunger axially movable with respect to the frame in a direction towards the mouth, from a rest position to a firing position, the apparatus having a mechanism configured to release the striker lock when the plunger reaches the firing position, allowing the striker to move from the retracted to the second position.

The striker may have resilient snap arms engaging a perimeter of the medical device to releasably hold the medical device in the striker; and the frame has ribs which contact the arms when the striker is in the first position to increase the force needed to release the medical device from the striker. The ribs may be fixed on the frame and extend longitudinally into the striker, touching the snap arms when the striker is in the first position.

The medical device may be rectangular and held in the striker by four of said snap arms, one acting on each corner of the medical device. The driver may be a spring longitudinally extending between the striker and the plunger, such as to compress as the plunger is moved from the rest position to the firing position. The striker lock may comprise an engagement between upstanding extensions on the frame and the striker, and the plunger may have a cam surface to dislodge the engagement.

The apparatus may further include: a retractor exerting a force on the needle in the direction to pull the needle out of the medical device; a releasable retractor lock preventing the retractor from pulling the needle out of the medical device; and a retractor lock release mechanism configured to release when the striker is in the second position and the plunger moves away from the firing position. The retractor may be a spring acting on a needle hub attached to the proximal end of the needle.

The plunger may comprise a push button head adapted to be gripped by the user merging via a shoulder portion to a wider diameter dependent skirt portion; and the apparatus further includes an external collar surrounding the frame and spaced therefrom to form an annular gap accommodating the dependent skirt of the plunger. The collar may be rotatable with respect to the plunger and there may be provided locking structures allowing axial movement of the plunger with respect to the frame at a given angular orientation. The locking structures may include a visible indication of the angular orientation at which the plunger can be axially moved.

The apparatus may further include a removable cover over the mouth of the frame to prevent access to the medical device and needle prior to use. The medical device may be a glucose sensor and the filament comprises sensor electrodes. The medical device may contain a wireless transmitter to transmit a signal representing measured glucose concentration to external equipment.

Provided is an apparatus for placing a medical device on the surface of the skin of a patient and inserting a medical filament extending from the device into the skin of the patient, comprising: a frame having a mouth for positioning against the skin during placement of the medical device, and an internal cavity for retention of the medical device prior to placement; the medical device having a surface adapted to be held against the skin of the patient and having the filament extending therefrom; a retractable needle extending through the medical device and carrying the filament; a striker holding the medical device and being axially movable within the frame from a first retracted position within the frame to a second position in which the surface of the medical device is presented at the mouth of the frame; a plunger being axially movable with respect to the frame in a direction towards the mouth; wherein the striker has resilient snap arms engaging a perimeter of the medical device to releasably hold the medical device in the striker; and the frame has ribs which contact the arms when the striker is in the first position to increase the force needed to release the medical device from the striker.

The apparatus may further include a removable cover over the mouth of the frame to prevent access to the medical device and needle prior to use. The medical device may be a glucose sensor and the filament comprises sensor electrodes. The medical device may contain a wireless transmitter to transmit a signal representing measured glucose concentration to external equipment.

BRIEF DESCRIPTION OF THE DRAWINGS

For a more complete understanding of the present disclosure, reference is now made to the following figures, wherein like reference numbers refer to similar items throughout the figures.

DETAILED DESCRIPTION

The following description and the drawings illustrate specific embodiments sufficiently to enable those skilled in the art to practice the system and method described. Other embodiments may incorporate structural, logical, process and other changes. Examples merely typify possible variations. Individual elements and functions are generally optional unless explicitly required, and the sequence of operations may vary. Portions and features of some embodiments may be included in, or substituted for, those of others.

Figure 1:
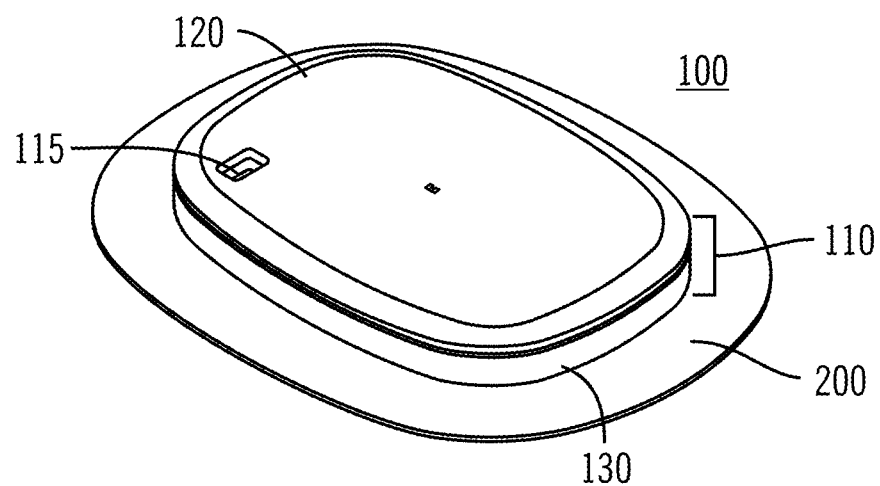
FIG. 1 illustrates a perspective view of a sensing device.

As shown in the exemplary drawings, an improved sensing device is provided for monitoring a body characteristic of the body. Also provided is an improved structure of the connections between the various components of the sensing device. One example body characteristic is the blood glucose level of the body. As shown in FIG. 1, a configuration of a sensing device 100 includes a housing 110 including an upper housing 120 with an upper major wall inside the upper housing, and a lower housing 130 with a lower major wall inside the lower housing, where the upper and lower major walls oppose each other. The housing 110 is shown as generally rectangular, but other shapes, such as rectangular (shown in other aspects herein), square shapes, circular shapes, polygon shapes, can be used according to the size of the components housed inside and to increase comfort levels on the skin. The housing has a low profile to decrease visibility through clothing and also to decrease discomfort and interference from the sensing device when it is worn on a patient's skin.

The housing may be attached to an adhesive patch 200 for press-on adhesive mounting onto the patient's skin. The patch may be sized such that it has as much adhesion to skin as possible while not being too large for comfort or to easily fit on a patient. The adhesive patch may be made out of a material with stretch to increase comfort and to reduce failures due to sheer. It is understood that alternative methods or techniques for attaching the mounting base to the skin of a patient, other than an adhesive patch, also may be contemplated. The housing 110 may be made out of a suitable rigid plastic that can safely and securely hold electrical components of the sensor. Suitable plastic materials include, as an example and in no way by limitation, ABS, nylon, an ABS/PC blend, PVC, polytetrafluoroethylene (PTFE), polypropylene, polyether ether ketone (PEEK), or the like, and polycarbonate. In this configuration, the upper housing 120 includes a small opening 115 for pass through of a battery pull tab (not shown) used to block the battery from contacting the electronic battery contacts prior to use, thus preventing battery depletion.

The adhesive patch may be bonded to the lower housing along the entire footprint of the lower housing, or over just a portion, such as the perimeter of the housing. Shear, tensile, peel, and torque loads are distributed as much as possible. The patch may be ultrasonically welded to the lower housing or adhered, for example, by a double-sided adhesive. In configurations, the adhesive patch extends further than the edge of the lower housing. In one configuration, the offset between the patch edge and the device edge is about 0.25 inches, although it may be smaller or bigger as long as it is conveniently sized to allow placement of the sensing device and to be comfortable on the skin of a patient.

Figure 2:
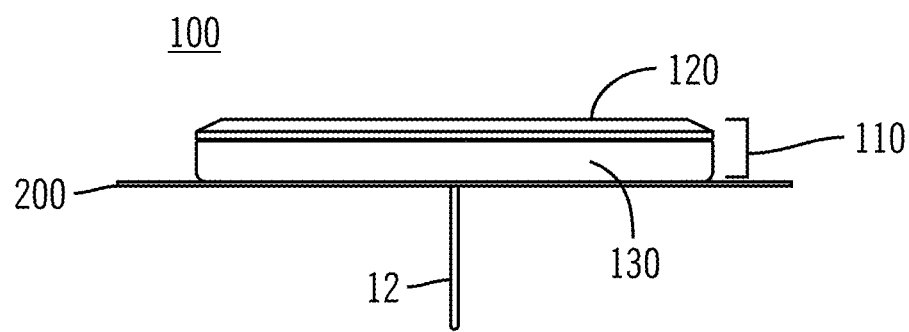
FIG. 2 illustrates a side view of a sensing device.
Figure 3:
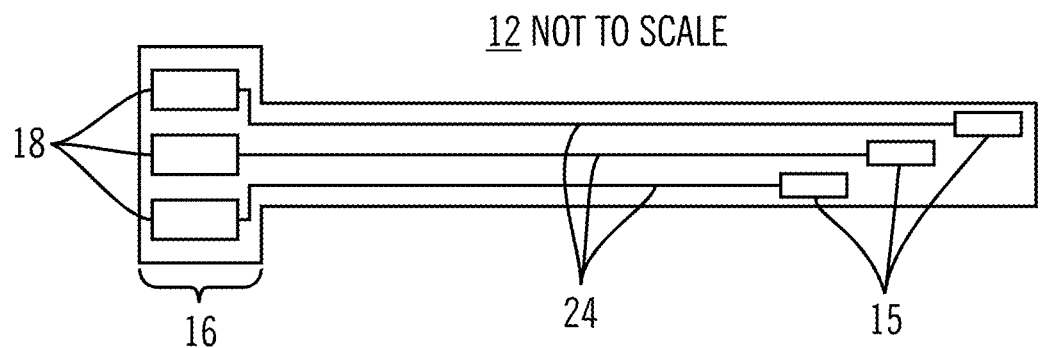
FIG. 3 illustrates a view of an analyte sensor.

FIG. 2 shows a side view of the sensing device 100 with thin film sensor 12 extending out of the housing through the patch 200, which may include a hole for the sensor 12 to pass through. The low profile/height of the housing 110 can be seen in FIG. 2. As shown in FIG. 3, the flexible thin sensor 12 comprises a relatively thin and elongated element which can be constructed according to so-called thin mask techniques to include elongated conductive elements 24 embedded or encased between layers of a selected insulative sheet material such as polyimide film or sheet. Support may be provided to the flexible thin sensor. For example, the flexible thin sensor may be contained in a flexible tube to provide support. However, it is possible for a thicker sensor to be stiff enough to facilitate sensor to base assembly and to reduce instances of sensor kinks without a flexible tube. A thickness of about 17-40 µm is sufficiently thick to provide this stability, for example 25 µm. The proximal end or head 16 of the sensor 12 is relatively enlarged and defines electrical contacts, the conductive contact pads 18, which are exposed through the insulative sheet material for electrical connection to the printed circuit board assembly containing and connected to the various electrical components of the sensor. An opposite or distal segment of the sensor 12 includes the corresponding plurality of exposed sensor electrodes 15 for contacting patient body fluid when the sensor distal segment is placed into the body of the patient. The sensor electrodes 15 generate electrical signals representative of patient condition, wherein these signals are transmitted via the contact pads 18 and connector, which includes sensor electronics (including a wireless transmitter) to an appropriate monitoring device (not shown) for recordation and/or display to monitor patient condition. Further description of flexible thin film sensors of this general type may be found in U.S. Pat. No. 5,391,250, which is herein incorporated by reference. Sensor electronics including wireless transmitters are discussed, for example, in U.S. Pat. No. 7,602,310, which is herein incorporated by reference.

Figure 4:
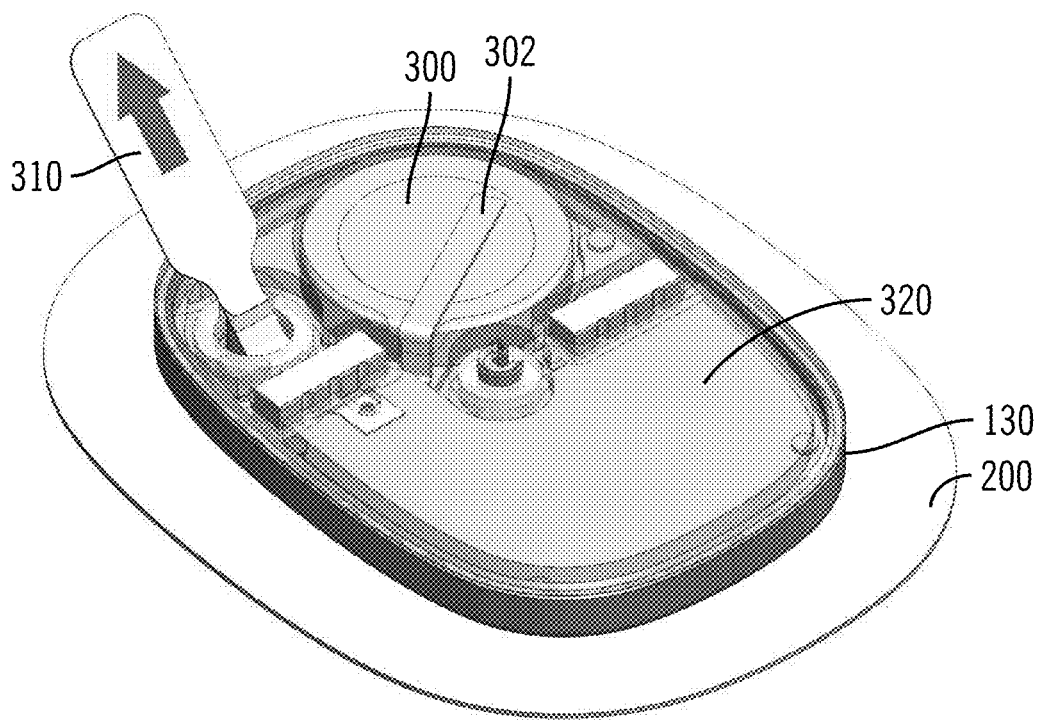
FIG. 4 illustrates an internal view of a sensing device.

As shown in FIG. 4, the lower housing 130 contains various electrical components. In various embodiments, the lower housing 130 is water tight to protect the components from water damage. A printed circuit board assembly (PCBA) 320 fits inside the lower housing 130 and is supported by one of the major walls (upper or lower housing). The PCBA is adapted to receive electrical signals from the sensor through electrical contacts on the PCBA. In the embodiment shown in FIG. 4, the PCBA fits in about two-thirds to three-fourths of the lower housing and is shaped such that a battery 300 fits next to, not on top of, the PCBA. Electrical components of the sensing device are electrically connected to the PCBA. Back to back sensors may be mounted directly to the PBCA. A battery 300 is included to provide power to the electronic components. In FIG. 4, the battery 300 is a coin cell battery, which is held using a battery clip 302. Any suitable battery that is small in size with sufficient life for the sensing device may be used. For example, if a CR3115 3V battery (48 mAh) is used, it has the capacity for 14-day wear. A battery pull tab 310 disconnects the battery 300 from the PCBA to prevent battery drain during shipping and storage. The user removes the pull tab 310 after inserting the sensor into the user's body, turning on the sensing device 100. Additional batteries may be used. For example, two or more batteries in series may be used instead of the one battery shown in FIG. 4.

Figure 5:
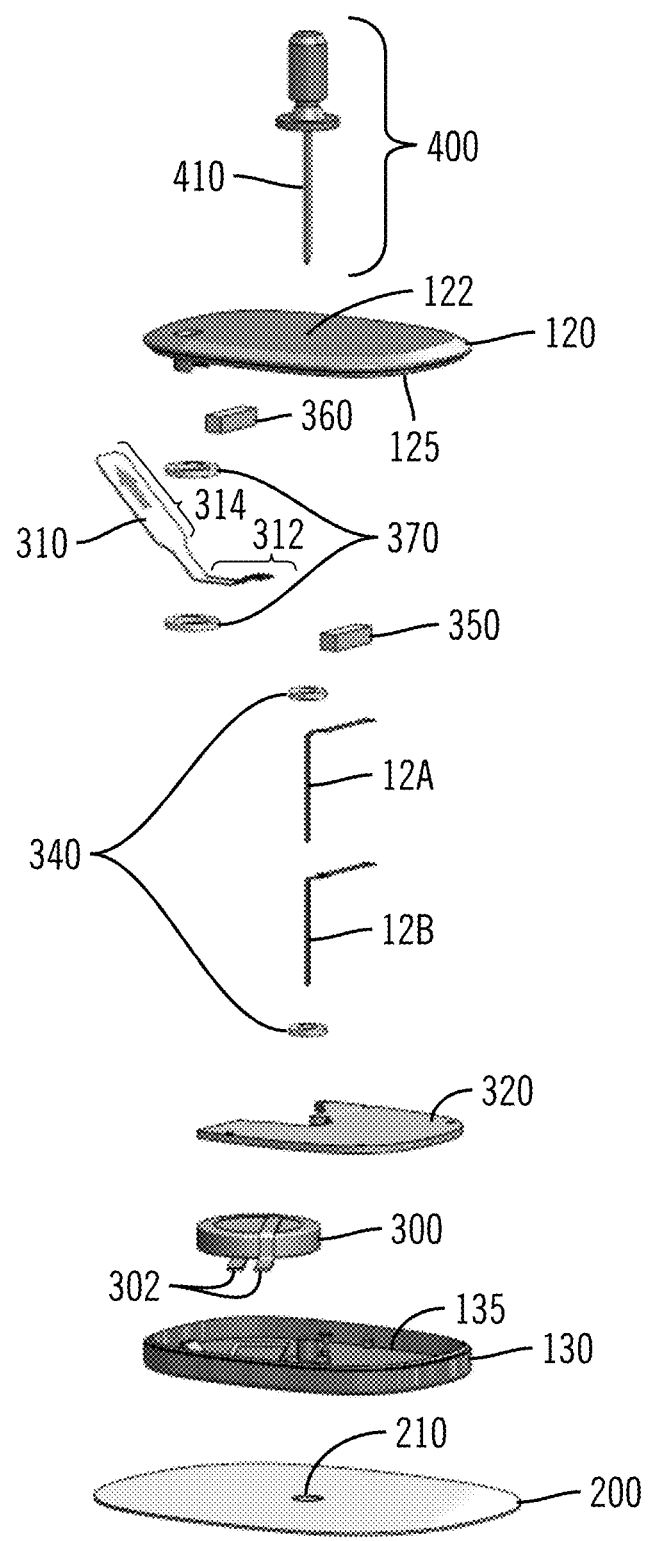
FIG. 5 illustrates an exploded view of a sensing device.

FIG. 5 shows an exploded view of one configuration of a sensing device 100. Upper housing 120 includes an interior upper wall 125 and needle opening 122. The adhesive patch 200 is below the components for attaching the sensing device 100 to the skin of a user. The lower shell/housing 130 has an interior lower major wall 135 and houses the electrical components, which include a battery 300 held into place by battery clip 302. Alternatively, the battery (or batteries) may be held into place by other methods such as integrated solder pads on a flex or rigid or rigid/flex circuit board. It is further possible to hold the battery in place by shaping the upper and/or lower housings in a way to confine the battery and prevent it from moving when the upper and lower housings are connected to each other. The PCBA 320 is electrically connected to the electrical components. In this configuration, two sensors (12A and 12B) are used in conjunction with each other. In other configurations, one sensor or more than two sensors may be used. Multiple sensors may sense the same or different characteristics of a user (e.g., glucose and vitamin levels). The sensors may include more than one electrode. In one aspect, each sensor is adapted to accommodate up to 5 electrodes. Potential configurations include one single-sided sensor, with up to five electrodes, two single-sided sensors, back-to-back, with up to five electrodes per sensor (the two sensors could be the same or different sensors), and one double-sided sensor, with up to five electrodes per side. In this aspect, each sensor may be about 0.060 inches by 0.900 inches, which allows housing of up to five electrodes. The sensor electrodes interact with contact pads on the PCBA, where the contact pads may be about 0.030 inches in diameter and may have a pitch of about 0.050 inches. Other sizes may be used that are suitable for a small sized sensing device.

The sensors 12A, 12B may be held in place by sensor elastomeric connector/elastomeric pad 350 and sealed using sensor gaskets 340. When the upper and lower housings are connected, and the PCBA is supported by the lower housing and lower wall, the elastomeric connector is biased by the upper housing and upper, opposing wall to urge the proximal end of the sensor into contact with the PCBA and maintain an electrical connection between the electrical contacts and the PCBA. Battery pull tab 310 is connected to the upper housing 120 using pull tab elastomeric connector 360 and sealed with pull tab gaskets 370. The base 312 of the battery pull tab blocks the battery 300 from electrically connecting to the PCBA 320. The battery pull tab upper portion 314 extends outside of the housing when the sensor is assembled so that a user can remove it to turn on the sensing device. A needle hub 400 is shown, with needle 410 to aid in insertion of the sensor into a user's body. The needle hub shown is a simple needle hub that houses the needle. A more complicated insertion tool may be included that utilizes the needle hub or as an alternative to the needle hub. The needle fits through the upper housing needle opening 122 and lower housing sensor opening (not shown) and patch sensor opening 210 when the sensor is inserted into the user's body. The needle hub 400 including the needle 410 can then be removed, leaving the sensor inside the user's body.

Figure 6:
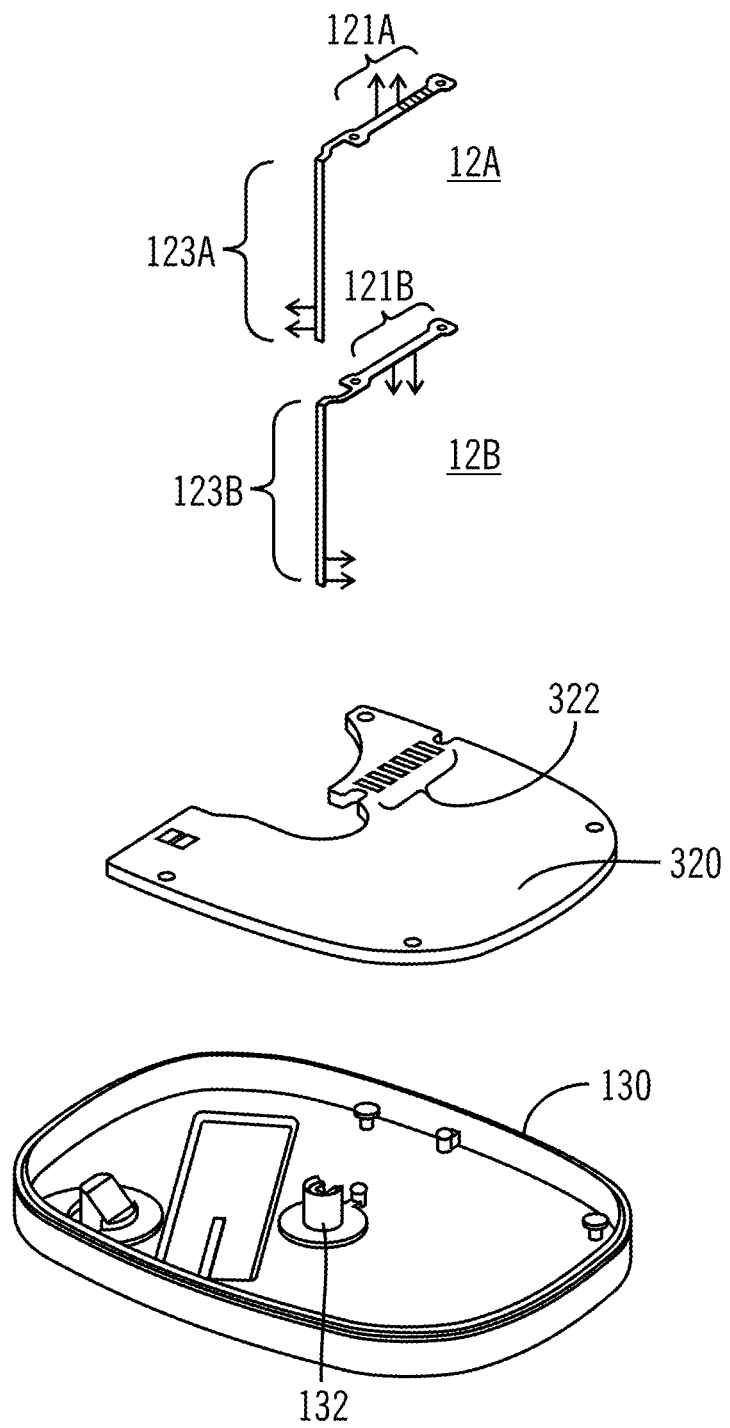
FIG. 6 illustrates an exploded view of components of a sensing device.

One configuration of sensors for use in the sensing device 100 is shown in an exploded view in FIG. 6. Upper sensor 12A has its contact pads 121A facing up and its sensor chemistry 123A facing left. Lower sensor 12B has its contact pads 121B facing down and chemistry 123B facing right. The PCBA includes PCBA sensor pads 322, which may be etched or deposited onto the PCBA such that the sensors will be electrically connected to the PCBA. The lower housing 130 shows lower housing sensor opening 132, through which the sensors 12A, 12B and, during insertion, a needle may extend. When the sensors are fitted into the housing with the remaining components, the sensor contact pads interact with the PCBA contact pads through direct touch connection. This direct connection allows for all of the sensor components to be housed within a single housing, unlike previous sensor sets where the sensor is indirectly connected to the PCBA containing the sensor electronics (separately housed from the sensor itself).

Figure 7A:
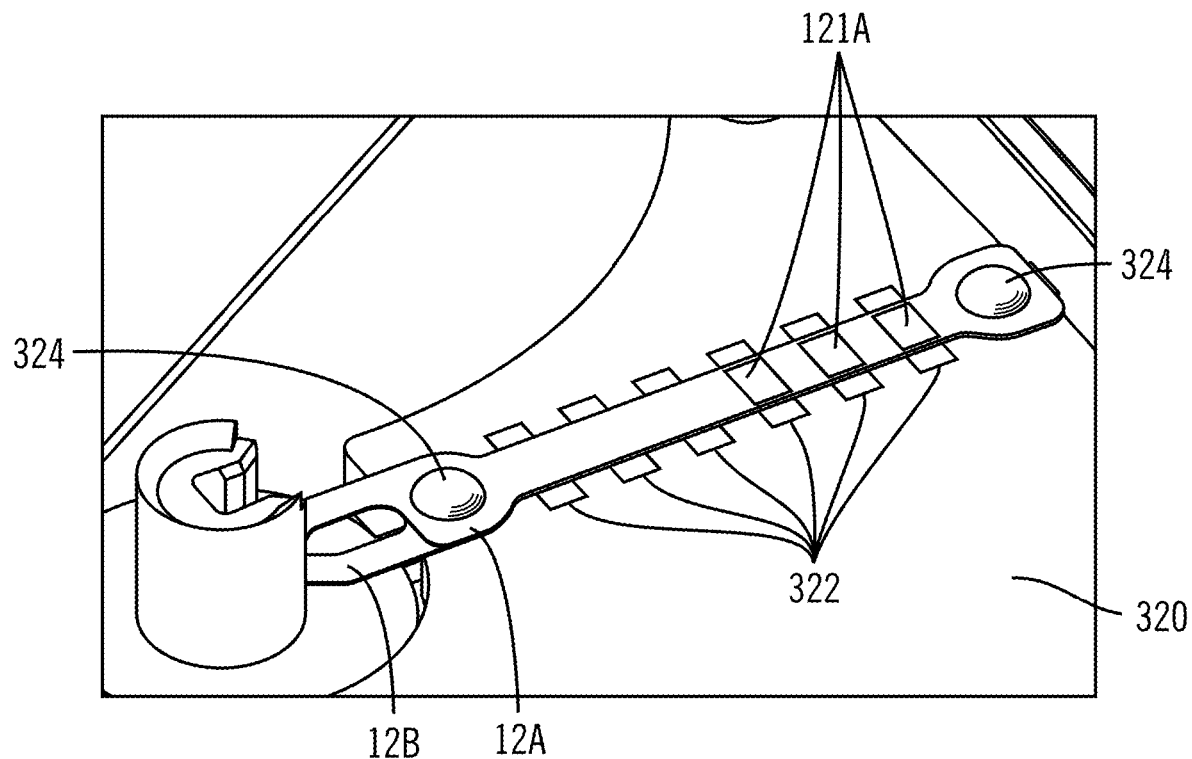
FIGS. 7A and 7B illustrate close up views of internal components of a sensing device.
Figure 7B:
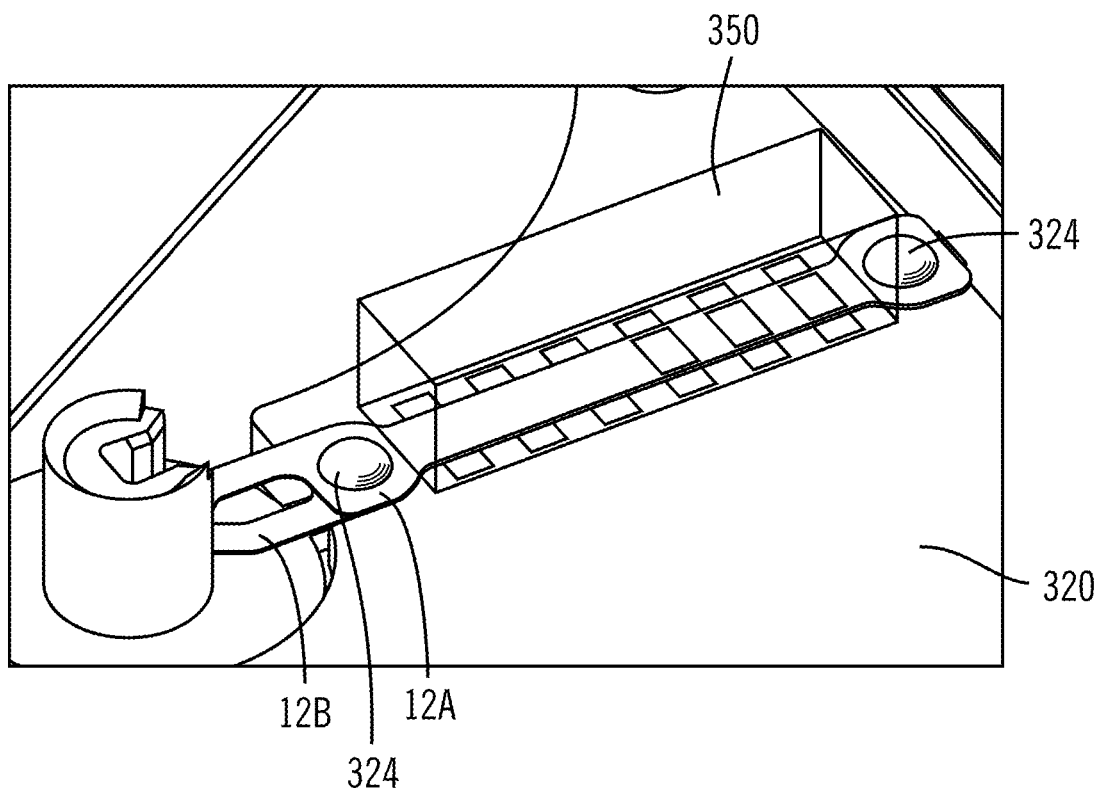

A more detailed view of the sensor electrical connections is shown in FIGS. 7A and 7B. As illustrated, in these partial views of the sensing device according to one or more embodiments, lower shell posts 324 locate the sensor pads so that they contact the PCBA sensor pads 322. FIG. 7B shows (transparently) the sensor elastomeric connector 350, which in this configuration is sandwiched between the upper housing and the sensors/PCBA. The sensor elastomeric connector 350 presses the lower sensor 12B against the PCBA sensor pads. The sensor elastomeric connector 350 electrically connects the upper sensor contact pads to the PCBA sensor pads.

Figure 8A:
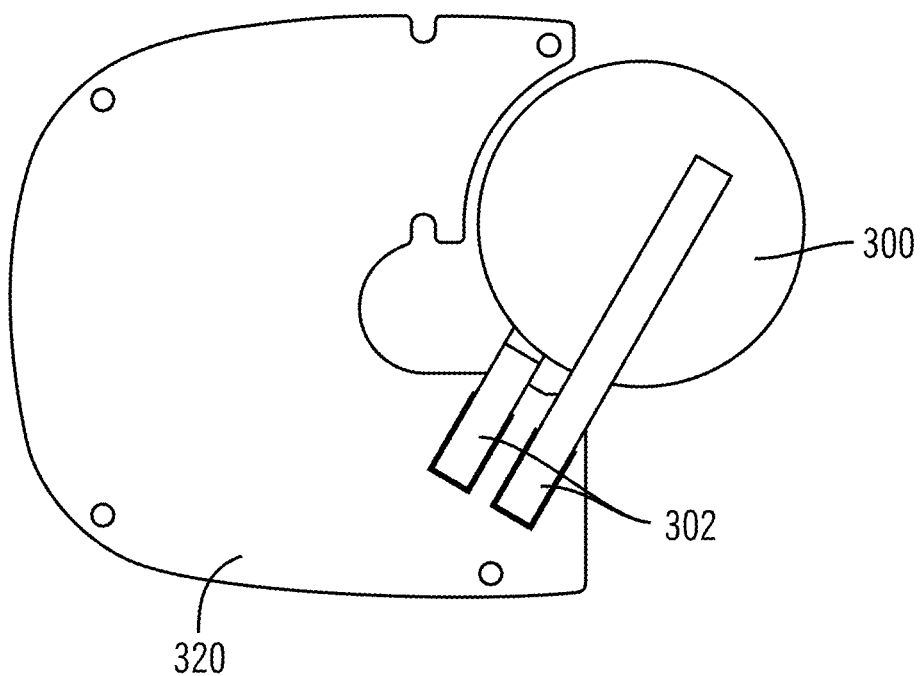
FIGS. 8A-8B illustrate top views of internal electrical components of a sensing device.
Figure 8B:
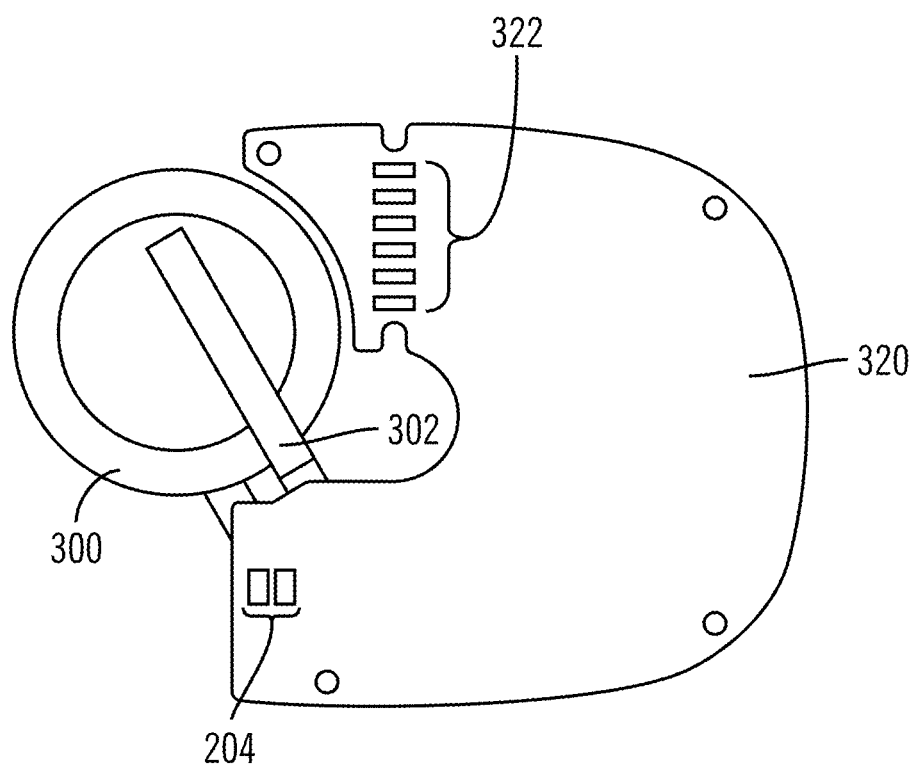
Figure 8C:
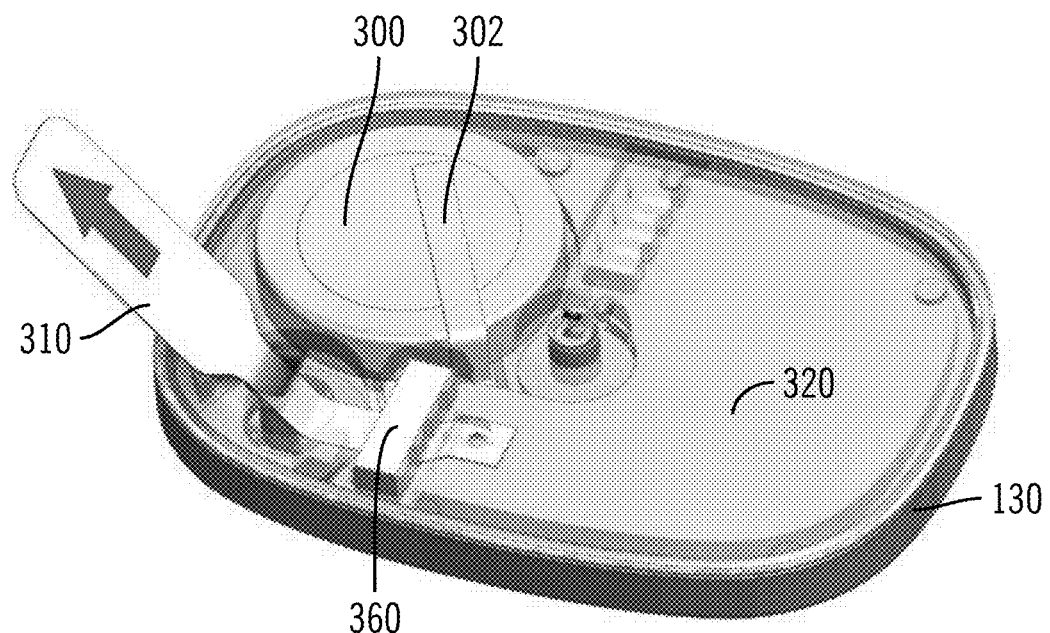
FIGS. 8C-8D illustrate perspective internal views of a sensing device.
Figure 8D:
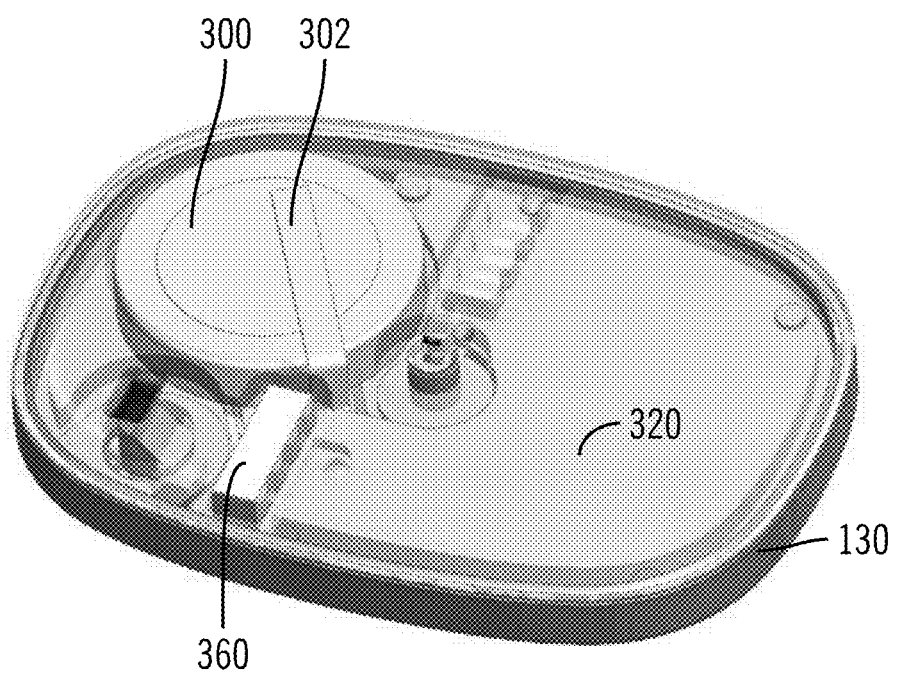
Figure 8E:
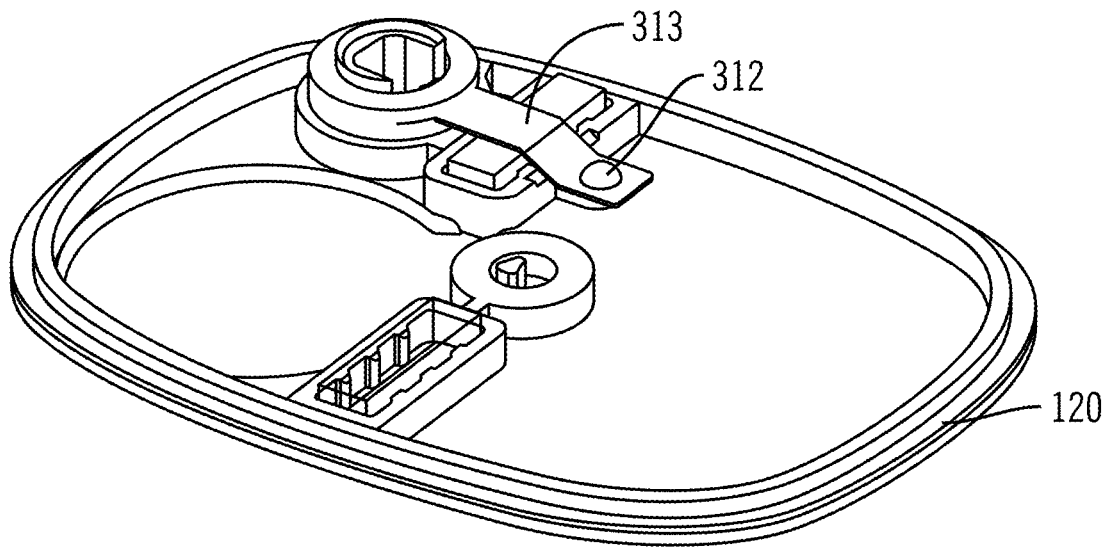
FIG. 8E illustrates a perspective view of an upper housing of a sensing device.

FIGS. 8A-E show a configuration of a battery disconnect procedure according to certain embodiments. FIG. 8A shows a bottom view of the PCBA 320 with the battery 300 held by battery clips 302, which may be welded to pads on the underside of the PCBA 320. FIG. 8B shows the same configuration but with a top view of the PCBA 320. The battery 300 is held by battery clips 302. Battery connector pads 204 on the PCBA are shorted together to connect the positive side of the battery 300 to the PCBA 320. In FIG. 8C, the battery pull tab 310 is shown. The battery pull tab 310 is a non-conductive tab according to one or more embodiments. It may be sandwiched between the pull tab elastomeric connector 360 and the PCBA battery connector pads (not shown). When the battery pull tab 310 is sandwiched in this position, it blocks the electrical connection between the battery and the PCBA. After the sensor is inserted, a user can remove the pull tab, allowing connection between the battery and the PCBA so that the sensing device turns on, as illustrated in FIG. 8D. FIG. 8E shows the inside of the upper housing 120. A pull tab retaining post 312 is provided inside the upper housing 120. The battery pull tab may be heat staked to the upper housing 120 at the pull tab retaining post 312. If the battery pull tab is heat staked to the pull tab retaining post 312, the battery pull tab may have a tear notch to help it tear free from the pull tab retaining post during removal. A strap 313 holds the elastomeric connector of the battery pull tab elastomeric connector 360 into the upper housing.

Figure 9:
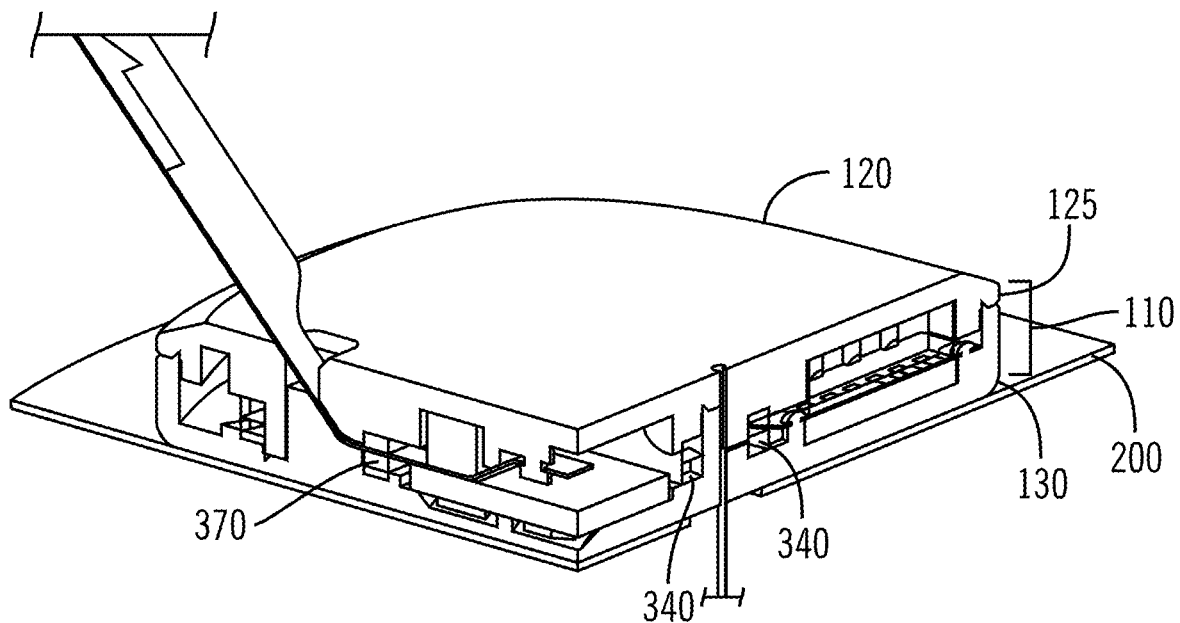
FIG. 9 illustrates a partial view of a sensing device.

The sensing device may be water resistant, with water tight seals provided between various external components, preventing potential damage to internal components from moisture. FIG. 9 illustrates a cut-away view of the sensing device 100. In one embodiment, the entire perimeter between the upper housing 120 and the lower housing 130 is sealed with an ultrasonic weld joint 125. Another type of welding or sealing of the upper and lower housing may be used as long as the connection is water tight enough to prevent the interior electrical components from being damaged. In general, it is not envisioned that the upper and lower housings will need to be separated from each other, because the sensing device is intended to be used once and disposed of. However, it would be possible to create another type of connection between the upper housing and lower housing for repair or replacement of parts in a more long-term sensing device. The pull tab gaskets 370 form face seals between the upper housing 120, lower housing 130, and battery pull tab 310. The sensor gaskets 340 form face seals between the upper housing 120, lower housing 130, and the sensors 12A, 12B.

Figure 11:
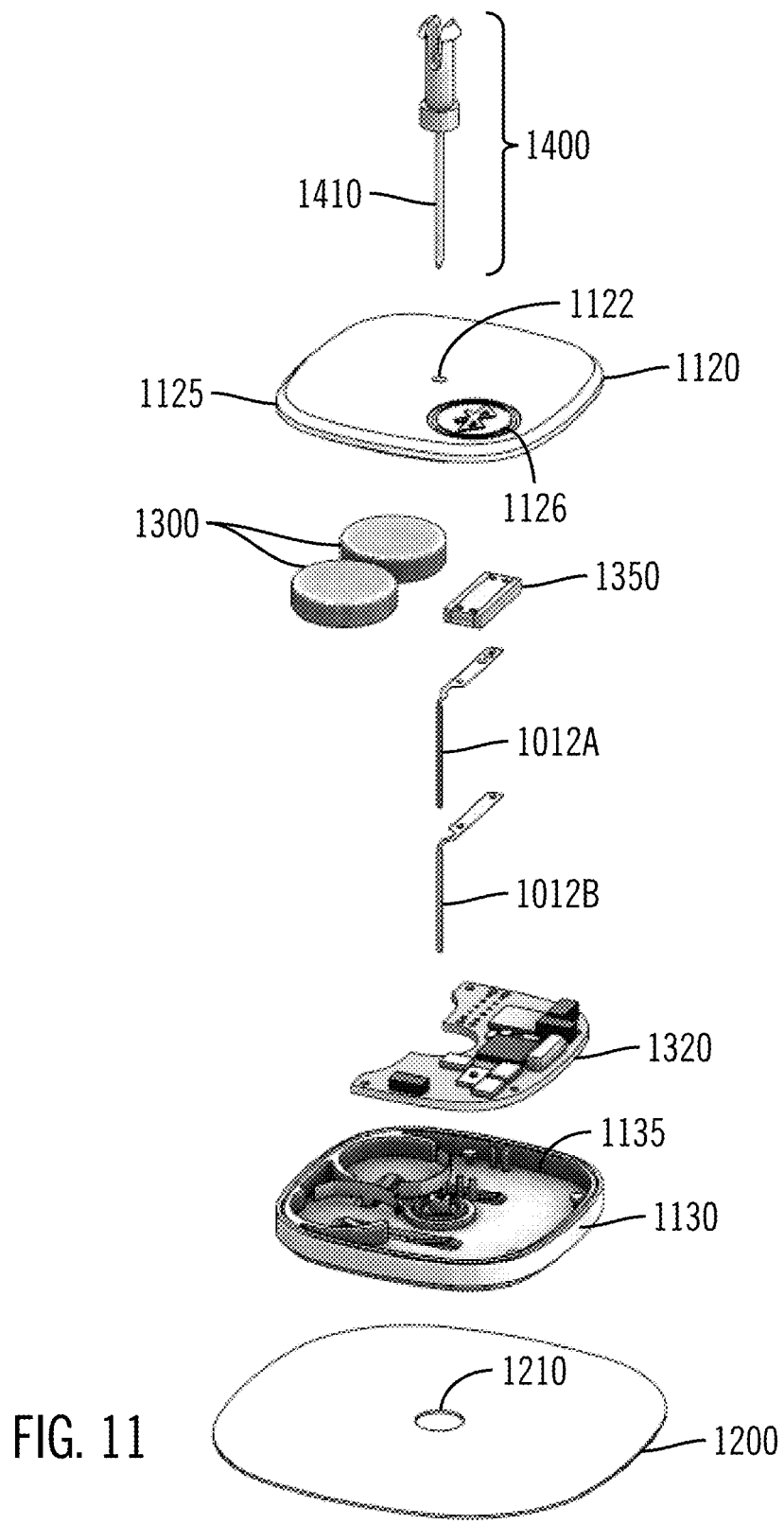
FIG. 11 illustrates an exploded view of a sensing device.

FIG. 11 shows an alternate configuration of a sensing device. Upper housing 1120 includes interior upper wall 1125 with needle hole 1122. The adhesive patch 1200 is below the components for attaching the sensing device to the skin of a user. The lower housing or shell 1130 with interior lower wall 1135 houses the electrical components, which include two batteries 1300. One battery or additional batteries may also be used. The batteries may be held in place by any method suitable for keeping them fixed within the housing. For example, they may be held into place by a battery clip. Alternatively, in the configuration shown, the batteries may be held into place by other methods such as integrated solder pads on a flex or rigid or rigid/flex circuit board. It is further possible to hold the battery in place by shaping the upper and/or lower housings in a way to confine the battery and prevent it from moving when the upper and lower housings are connected to each other. The PCBA 1320 is electrically connected to the electrical components. In this configuration, two sensors (1012A and 1012B) are used in conjunction with each other. In other configurations, one sensor or more than two sensors may be used. Multiple sensors may sense the same or different characteristics of a user (e.g., glucose and vitamin levels). The sensors 1012A, 1012B may be held in place by sensor elastomeric connector 1350. A needle hub 1400 is shown, with needle 1410 to aid in insertion of the sensor into a user's body. The needle fits through the upper housing needle opening 1122 and lower housing sensor opening (not shown) and patch sensor opening 1210 when the sensor is inserted into the user's body. The needle hub 1400 including the needle 1410 can then be removed, leaving the sensor inside the user's body. A push button 1126 is shown in the upper housing 1120. The push button may be used to turn on the sensing device, as set forth in the description herein. The particular push button configuration shown is an example configuration. It could be shaped in a different form, such as a circle. It could extend further than the housing or be configured so that its top surface is lower than the housing.

Figure 12:
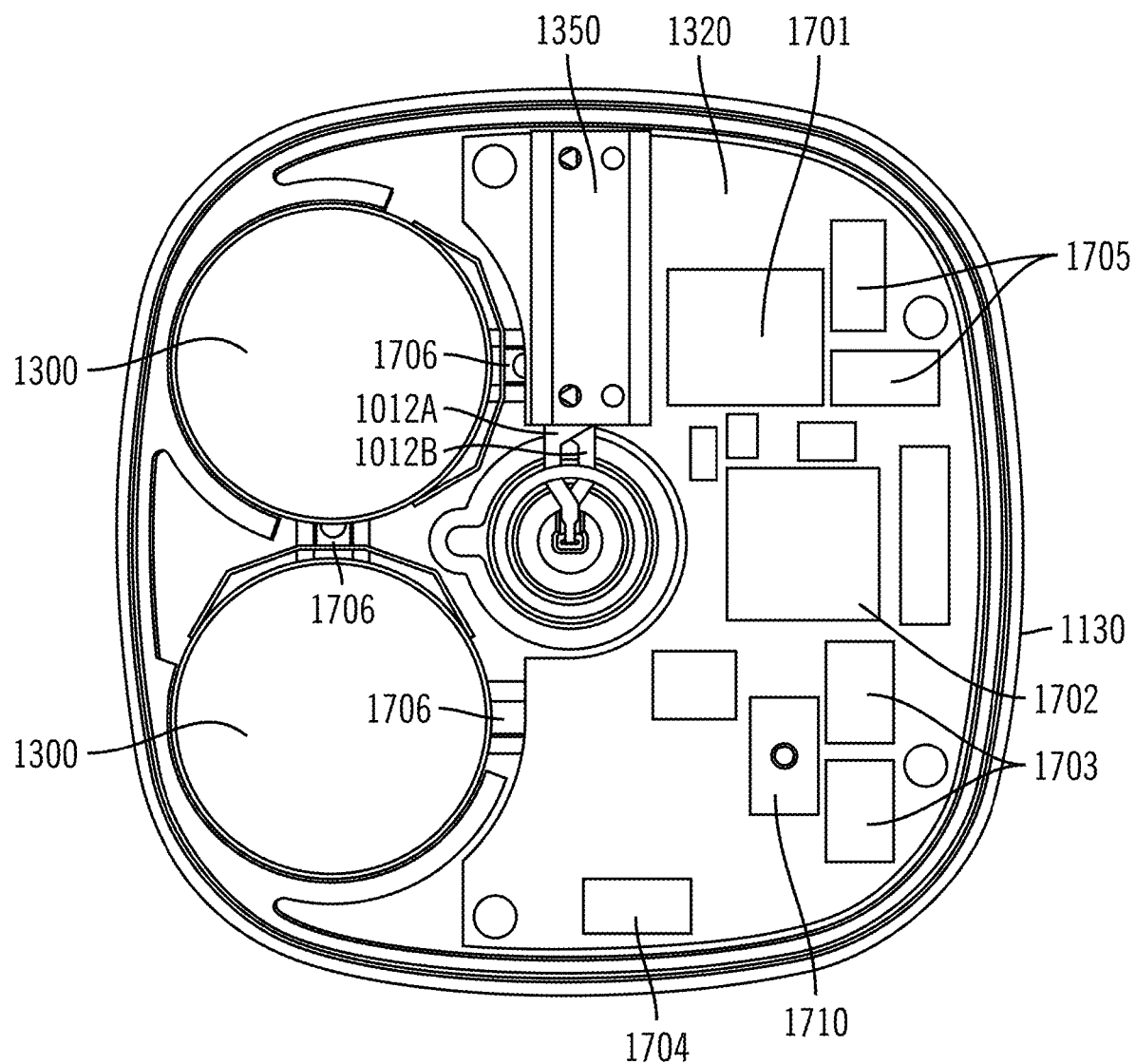
FIG. 12 illustrates top views of internal components of a sensing device.

FIG. 12 shows the configuration of FIG. 11 from a top view. The lower housing 1130 holds PCBA 1320 and batteries 1300. The sensors 1012A and 1012B are attached to the PCBA 1320 using elastomeric connector 1350. Also shown in FIG. 12 are electrical components that may be included in any configuration, including those discussed herein. The electrical components include ASIC (application specific integrated circuit) 1701, MCU (multipoint control unit) 1702, memory 1703, antenna 1704, and reservoir caps 1705. Battery tabs 1706 lead from the batteries 1300 to the PCBA 1320.

The battery tabs 1706 shown are part of three battery spring contacts, which may be heat staked or otherwise attached to the lower housing 1130. The battery spring contacts connect the two batteries together and to the PCBA. The connection to the PCBA may be on the underside of the PCBA so that the tabs are compressed by the PCBA when the PCBA is in the lower housing.

A power/pairing switch 1710 is included in this configuration that allows for turning on the sensing device using a button (not shown) that will be attached or housed in to the upper housing (not shown). It is also possible for the upper housing to be compressible such that when it is compressed, the switch 1710 is activated, turning on the sensing device. In this case, the use of the push button/switch is potentially an alternative to the battery pull tab discussed above. The sensing device may be configured such that the push button/switch only turns on the sensing device. Alternatively, it may be possible to turn off the sensing device using the push button/switch as well. The push button/switch may be used in addition to the battery pull tab. For example, it may be required to first remove the battery pull tab and then to activate the push button/switch in order to activate the sensing device.

In further configurations, the sensing device may be configured to be in a low power sleep mode prior to activation. When the battery is connected to the PCBA, the sensing device enters the low-power sleep mode. In the low-power sleep mode, the sensing device may be set up to periodically monitor the push button. When the push button is detected, the device would wake up fully and become fully activated. A push button may have multiple functions. It may wake up the sensor from a low-power shelf mode after insertion of the sensor into the body. It may initiate Bluetooth low energy or other pairing with a monitoring or other device. It may initiate data upload after sensor wear. Other potential uses are also contemplated by the button depending on the desired function of the sensing device. The button is formed in a way that is generally watertight. In certain aspects the materials of the button itself are selected to create a chemical bond for watertightness. For example, thermoplastic polyurethane may be overmolded onto the upper housing. A flexible, watertight material like this allows for depression of the button while retaining the watertight seal of the housing.

Figure 13:
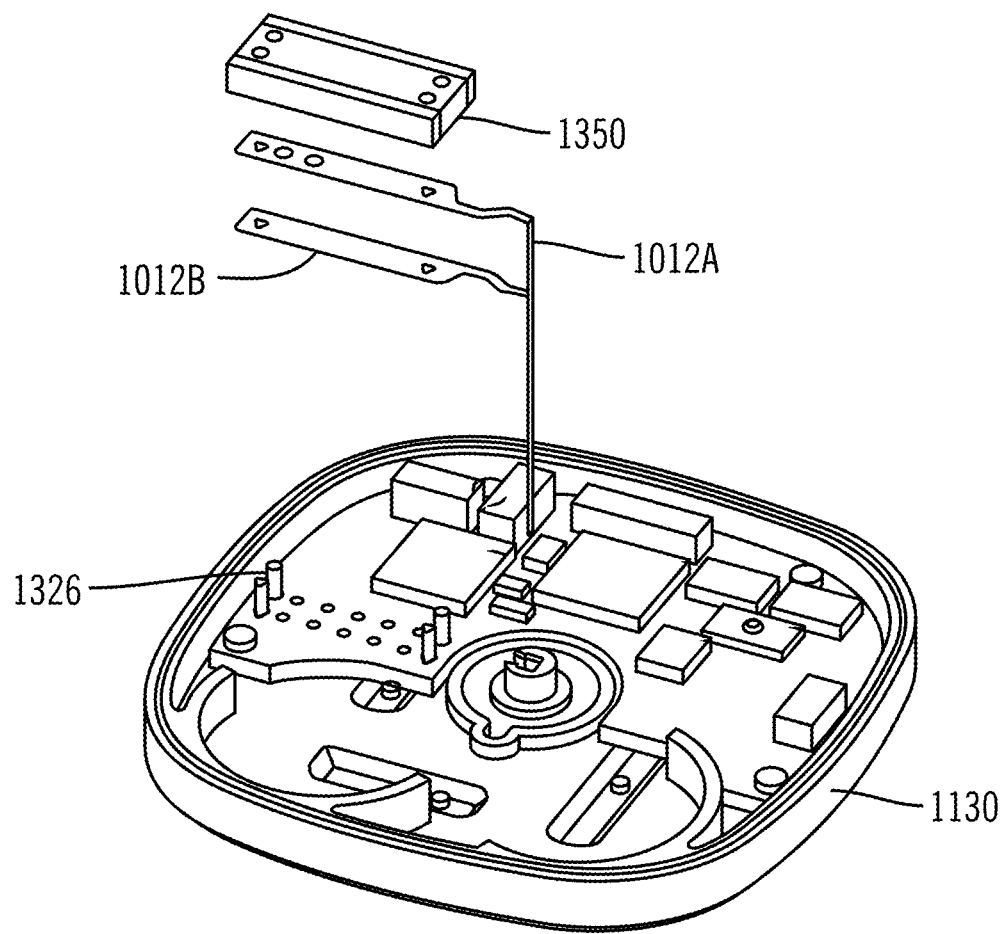
FIG. 13 illustrates a perspective, exploded view of components of a sensing device.

FIG. 13 shows a partially exploded view of the same configuration shown in FIGS. 11 and 12. The lower housing 1130 houses the PCBA 1320 with the various electrical components shown in FIG. 12. Upper sensor 1012A and lower sensor 1012B are configured to be attached to the PCBA at the upper sensor pads 1323 and lower sensor pads 1324. Locating posts 1326 are connected to the lower housing 1130 or the PCBA 1320 and are placed to locate the sensors in the correct position with respect to the sensor pads. Elastomeric connector 1350 pushes the sensors onto the PCBA and may similarly contain openings for the locating posts 1326. The locating posts may be formed in an asymmetric manner, so that the sensors can only be placed in one manner, error-proofing sensor placement. The locating posts may be formed on the lower housing and go through holes in the PCBA, or they may be built into or onto the PCBA itself.

Figure 14A:
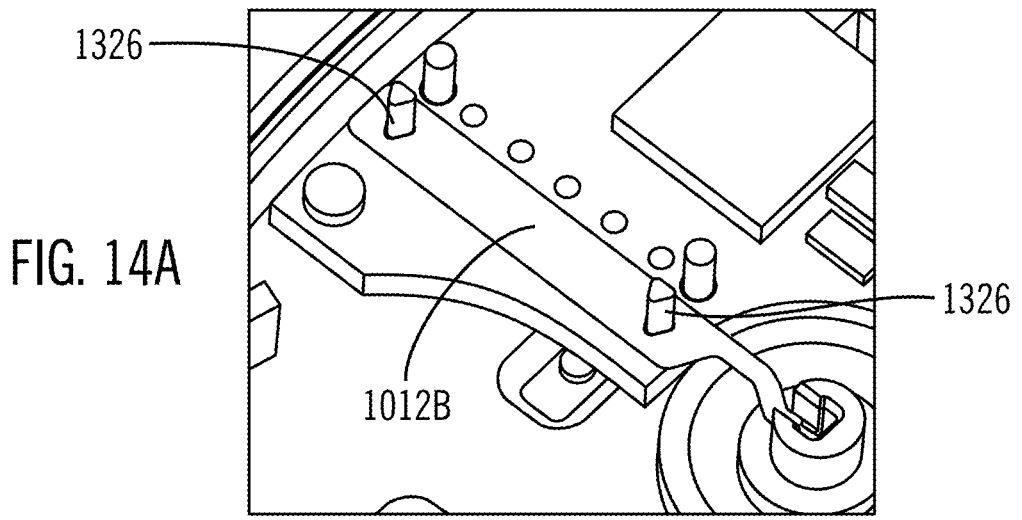
FIGS. 14A-14C illustrate partial views of internal components of a sensing device.
Figure 14B:
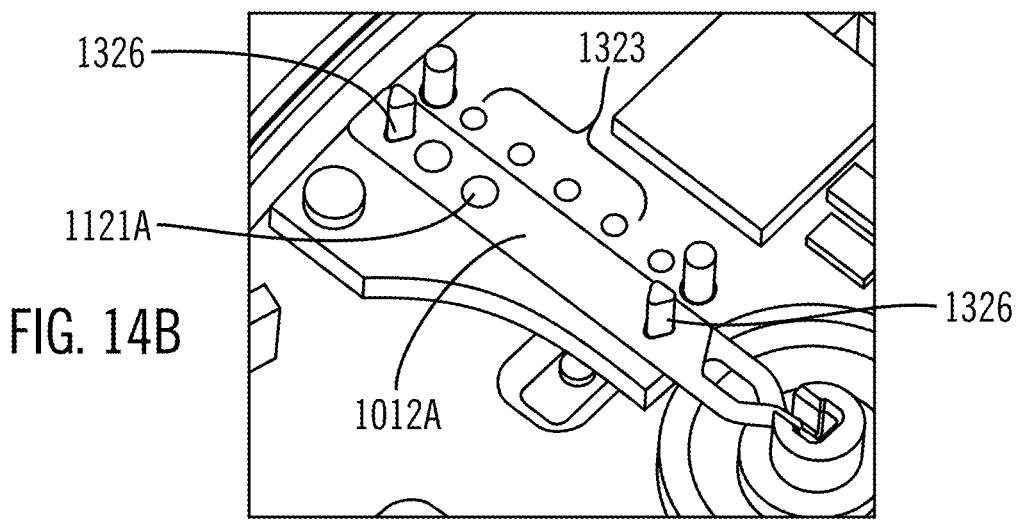
Figure 14C:
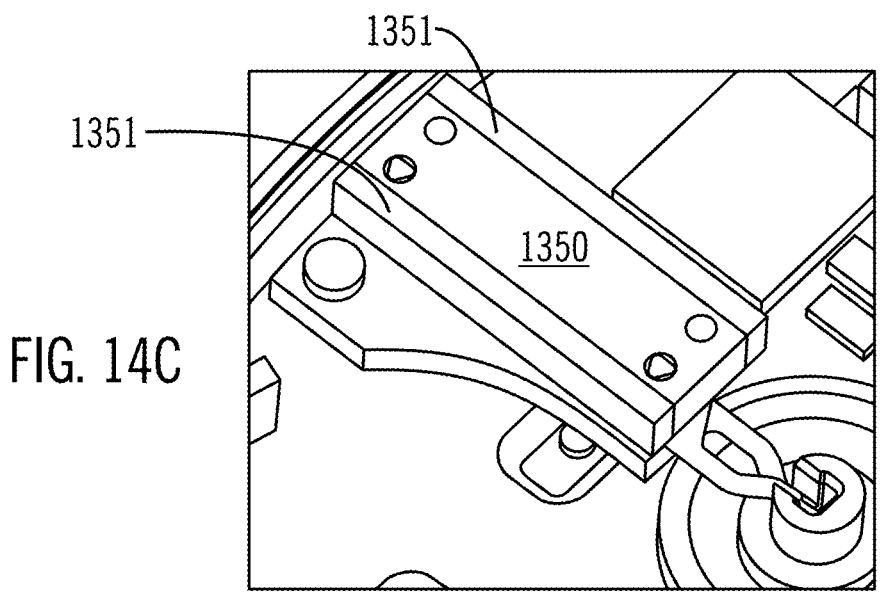

FIGS. 14A-14C show a more detailed view of the dual sensor configuration of FIG. 13. In the configuration shown, the lower sensor 1012B includes contact pads (not shown) on its bottom, which are compressed against the PCBA sensor pads. FIG. 14A shows only the lower sensor on the PCBA. Upper sensor 1012A is shown in FIG. 14B with its contact pads 1121A adjacent to PCBA contact pads 1323. In FIG. 14C, the elastomeric connector 1350 has been compressed against the PCBA by the upper shell. The elastomeric connector 1350 connects the upper sensor pads to the PCBA contact pads and compresses the lower sensor pads against the PCBA contact pads. In certain configurations, the elastomeric connector includes integral insulation layers 1351 on its sides. By creating this type of direct, touch connection between the sensor contact pads and the PCBA contact pads, it is possible to create a sensing device with a single housing, thus creating all the benefits of such a device that are discussed herein.

Figure 31:
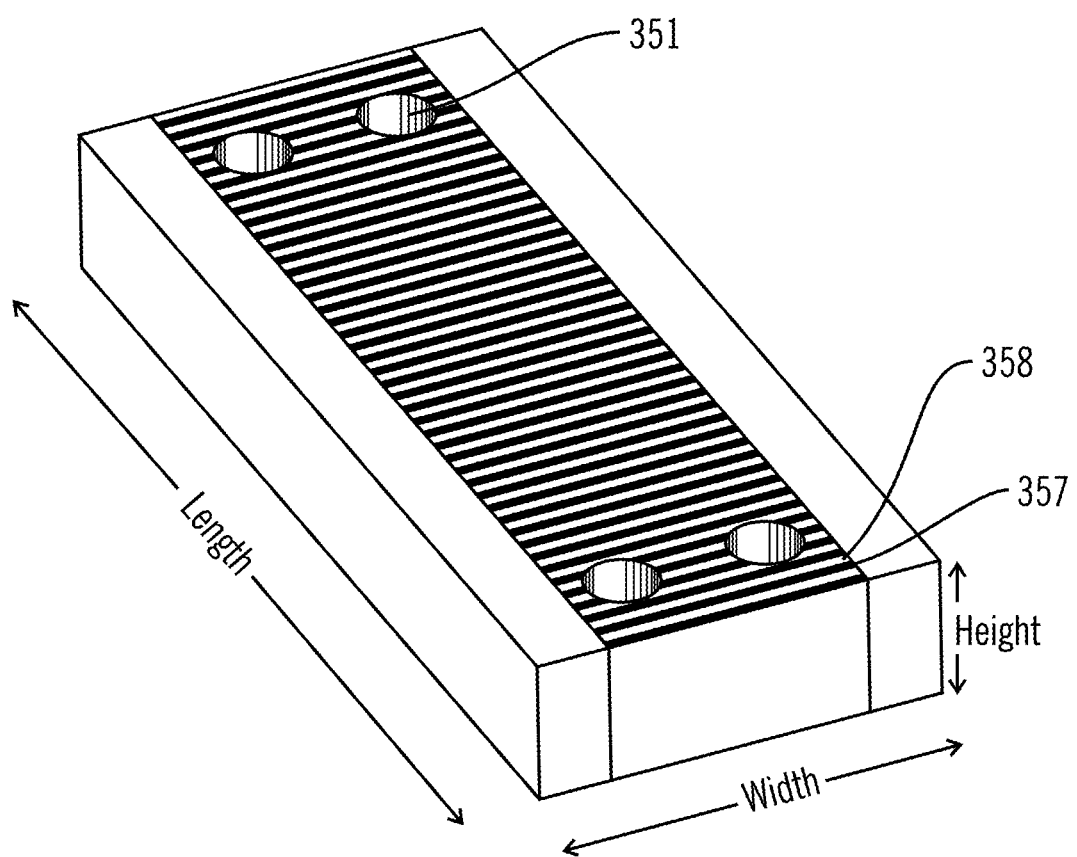
FIG. 31 illustrates an elastomeric connector of a sensing device.

The sensor elastomeric connector/pad 1350, also shown in FIG. 31 as reference number 350, includes alternating conductive layers 357 and non-conductive layers 358 (see FIG. 31) along its length, such that the elastomeric connector is conductive along its width and height but not along its length. Elastomeric connectors such as elastomeric connector 350 or 1350 are sometimes known as Zebra connectors. When placed on top of the lower sensor 1012B, the elastomeric connector applies pressure through the upper sensor 1012A to the lower sensor 1012B, connecting the lower sensor pads directly to the PCBA sensor pads. The sensor polyimide or other flexible insulative material insulates the lower sensor pad from the upper PCBA sensor pad. The elastomeric connector connects the upper sensor pad to the upper PCBA sensor pad, and the sensor polyimide (or other flexible insulative material) isolates the lower sensor pad from both the upper sensor pad and the upper PCBA sensor pad. Mounting holes 351 (see FIG. 31) are provided for mounting the elastomeric connector on the locating posts on the PCBA.

The electrical contacts of the lower sensor face the contact pads on the PCBA, and the elastomeric connector/pad, presses the electrical contacts on the sensor into touching connection with corresponding contact pads on the PCBA to maintain the electrical connection. The electrical contacts on the upper sensor face away from the PCBA, the PCBA having contact pads displaced to the side of the sensor, and the elastomeric connector/pad containing conductive strips positioned to connect electrically the contact pads of the PCBA to respective electrical contacts of the sensor to maintain the electrical sensor.

Figure 15:
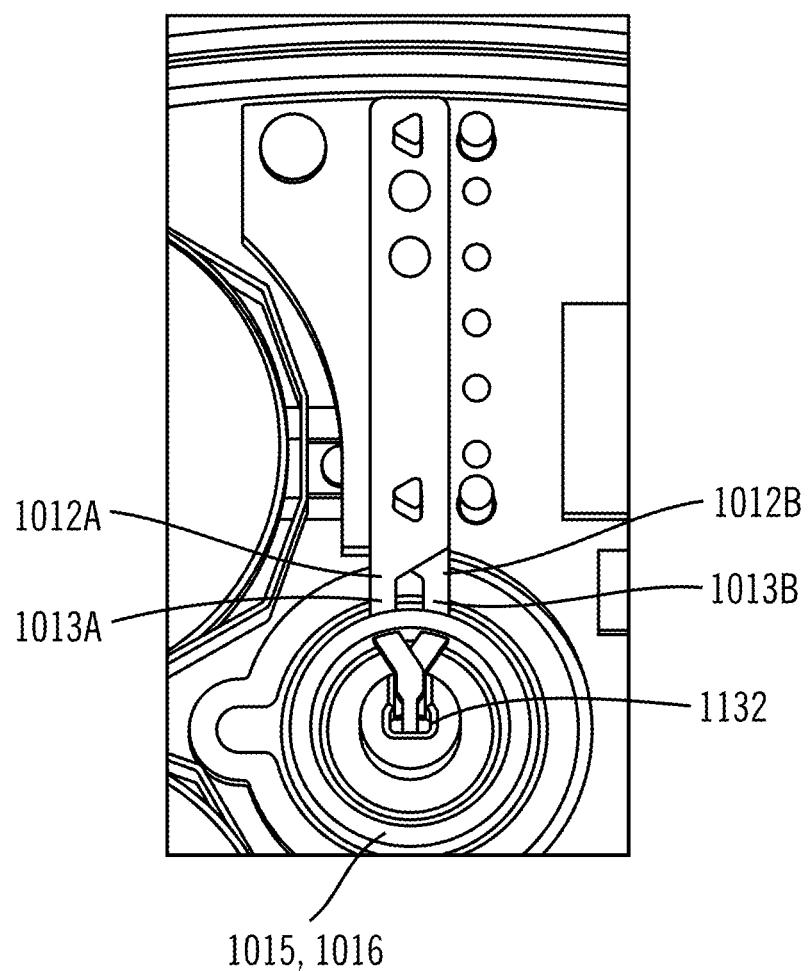
FIG. 15 illustrates a partial view of internal components of a sensing device.

The sensors may be sandwiched between gaskets to form a watertight seal. As shown in FIG. 15, gaskets 1015, 1016 surround the upper sensor 1012A and 1012B near the opening 1132 in the lower housing that allows the sensors to exit the housing for insertion into the body of a patient. The gaskets may be made out of thermoplastic polyurethane, for example, and may be overmolded onto the upper housing and the lower housing. In configurations, the sensor legs 1013A and 1013B that extend through the lower housing sensor opening 1132 are staggered to avoid a double layer of sensors (which may be made from polyimide) at the seal location. By staggering the sensors in this way, the gaskets can achieve a tighter configuration, decreasing likelihood of any leakage. The sensors can be clamped down near the lower housing sensor opening 1132 to prevent pull ups. In certain configurations this lower housing sensor opening is shaped to accommodate various needle profiles so that different insertion tools may be used when inserting the sensor into a patient's body.

Figure 16A:
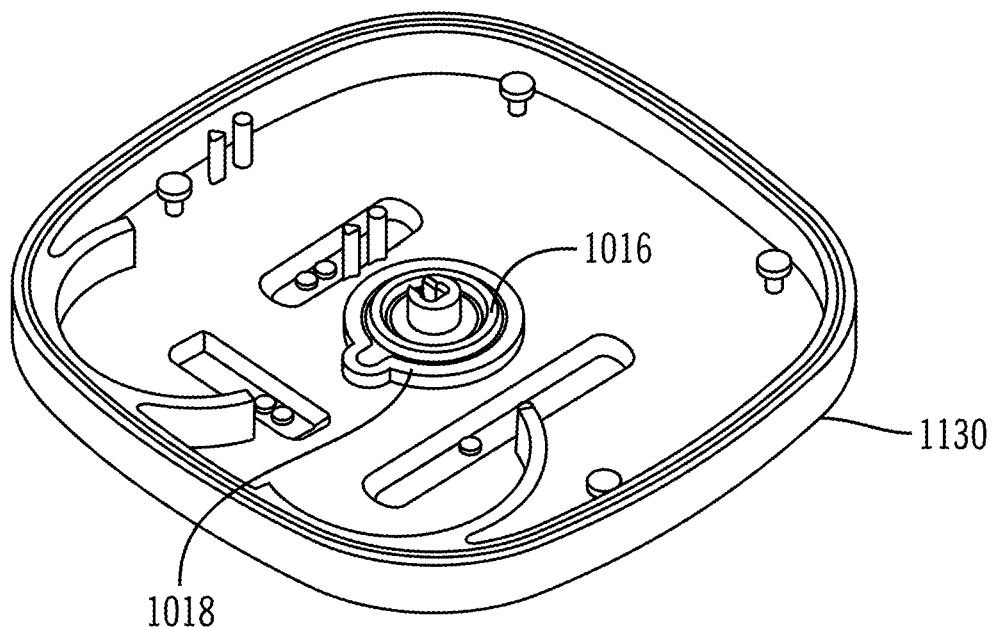
FIGS. 16A and 16B illustrate perspective views of portions of a sensing device.
Figure 16B:
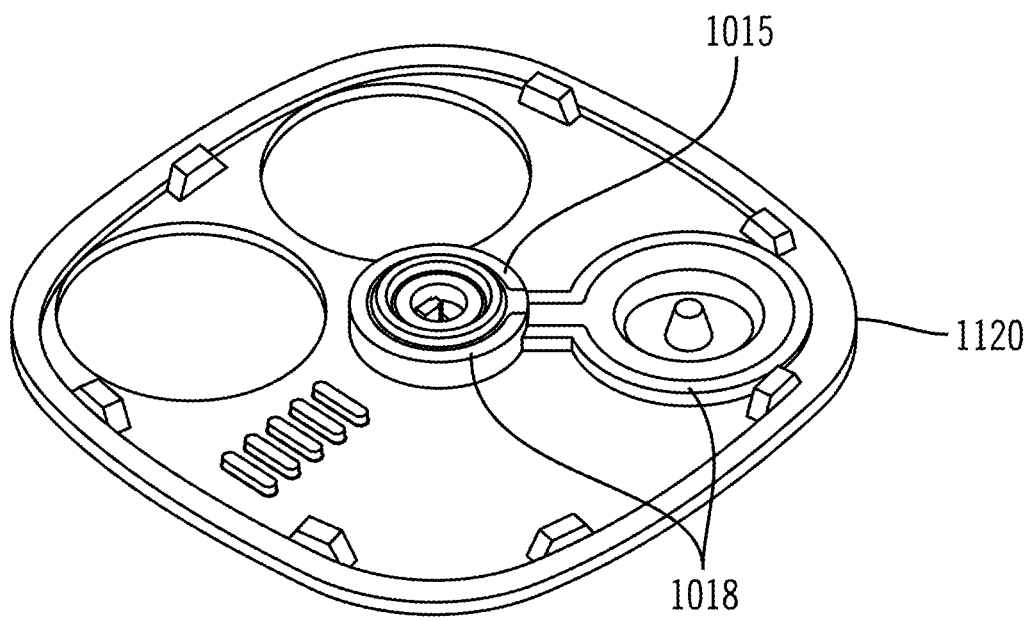

The formation of the gaskets is shown in more detail in FIGS. 16A and 16B. Lower gasket 1016 is formed in lower housing 1130, and upper gasket 1015 is formed in upper housing 1120. The sensor gaskets may be overmolded onto the housings and are surrounded by shutoff surfaces 1018.

The sensors 12A and 12B may comprise two strips of insulative sheet material, each having on its surface elongate conductive elements leading from the distal end to the contacts at the proximal end, wherein the strips are arranged back-to-back such that the contacts on one strip face towards the PCBA and the contacts on the other strip face away from the PCBA. The sensors may extend from the housing/case via an opening in the lower housing and lower major wall, there being a seal separating the opening from an internal cavity of the case housing of the PCBA, said seal being held in compression between the upper and lower housings, wherein the back-to-back strips separate to a side-by-side relationship where they pass through the seal.

Figure 10A:
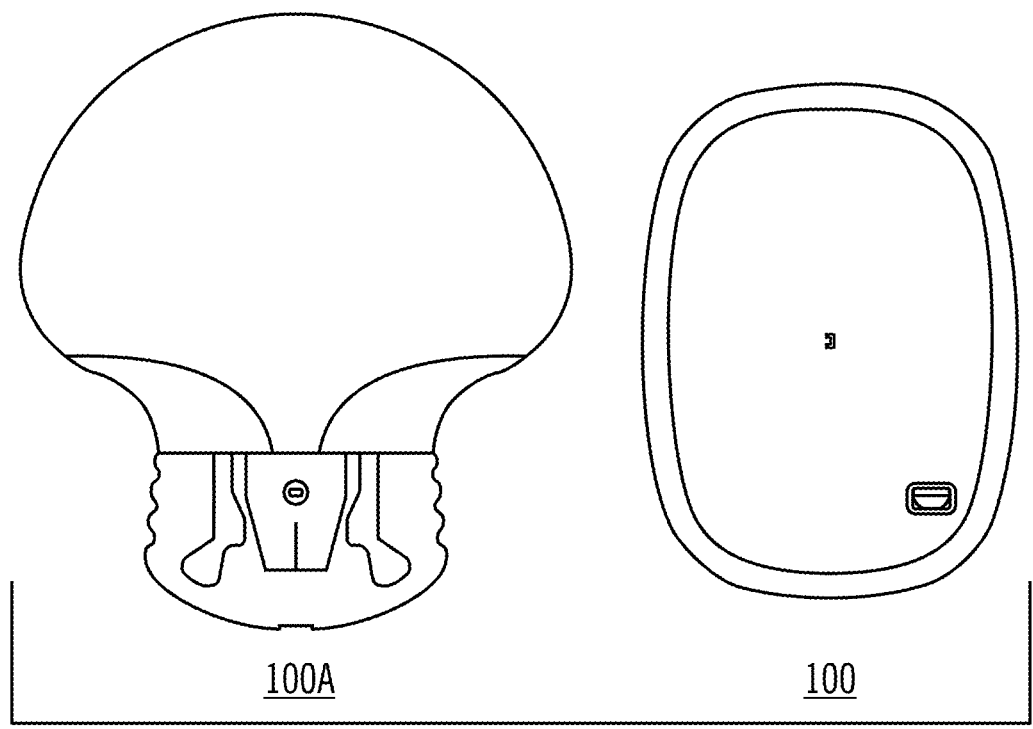
FIGS. 10A-10B illustrate views of a prior art sensing device and a sensing device according to an embodiment described herein.
Figure 10B:
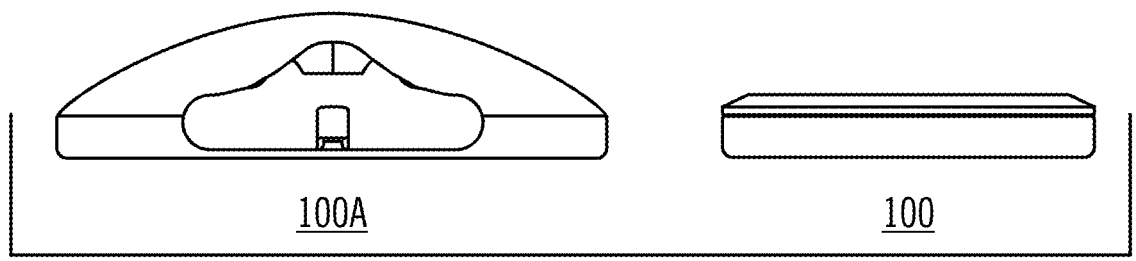

By reducing the components of the sensing device to a single housing, as opposed to earlier models where the sensor base is separate from the sensor electronics/transmitter, it is possible to greatly reduce the on-body device size. For example, FIGS. 10A and 10B show a comparison of an earlier, two-piece model 100A with a model 100 according to an embodiment. As can be seen, from both the top view FIG. 10A and side view FIG. 10B, the integrated sensing device greatly reduces size in all directions. It is thinner, and has substantially less volume. For example, the presently disclosed device according to one or more embodiments may be about the thickness of two stacked nickels, which is about 4 mm, or even thinner (e.g., about 3 mm) and is about 50% thinner and about 50% less in volume than current multi-part sensor sets. By reducing the on-body device size, user comfort is greatly increased.

Figure 17:
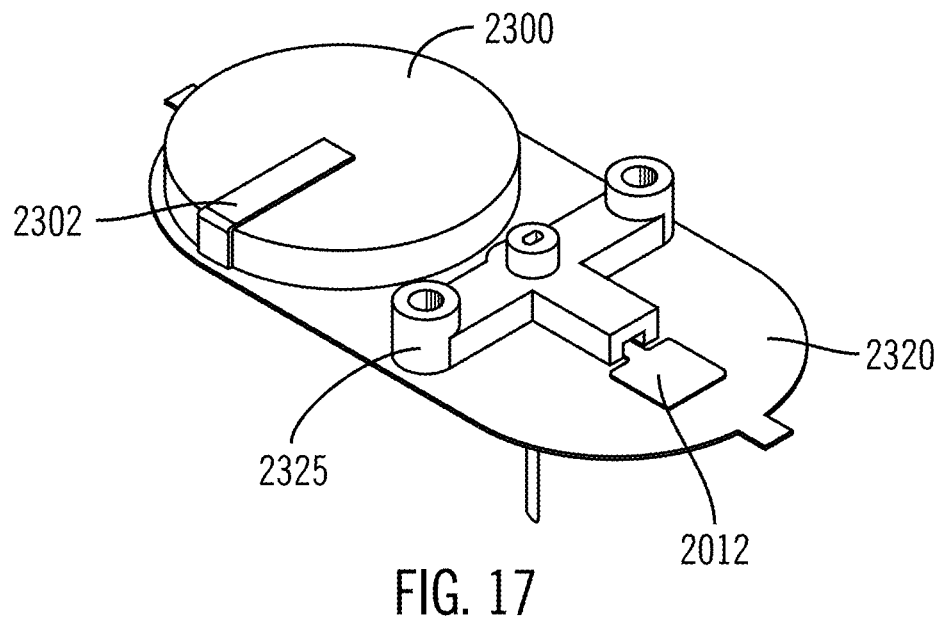
FIG. 17 illustrates a perspective view of internal components of sensing device.
Figure 18:
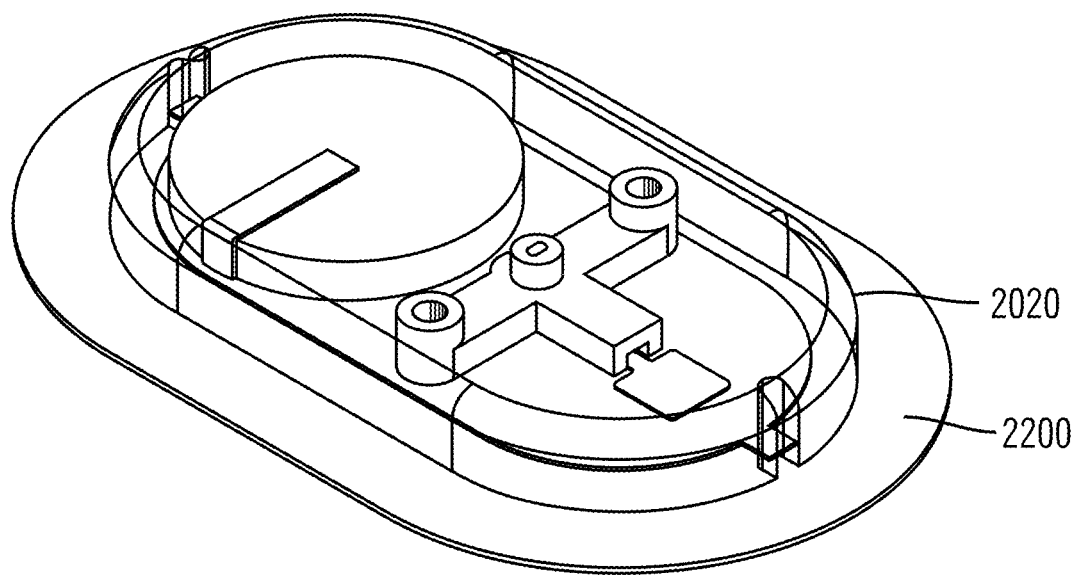
FIG. 18 illustrates a perspective view of a sensing device, with the external housing shown as transparent.
Figure 19:
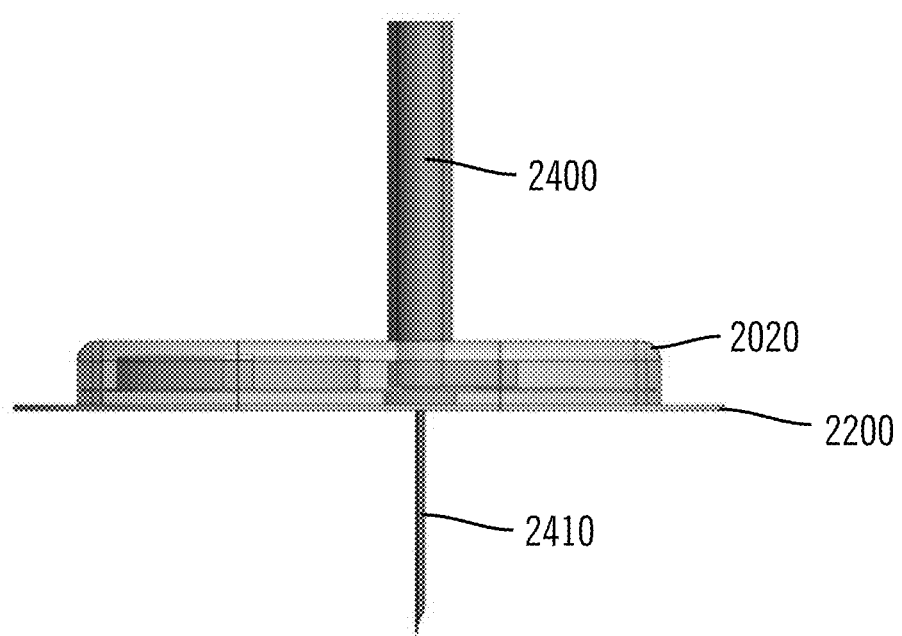
FIG. 19 illustrates a side view of a sensing device, with the external housing shown as transparent.

In another aspect, a very simple sensor is provided. As shown in FIGS. 17-19, an adhesive bandage type configuration may be used, where the entire sensing device has a smaller footprint than a standard size adhesive bandage, for example less than 3 inches by 1 inch. This configuration may include a housing shape that is generally rectangular, where the shorter sides are semicircular and the long sides are parallel, straight sides, the body being of uniform height. In other aspects, the housing shape may be of any appropriate shape for wearing or use by a user, for example circular, square, polygon, etc. The configuration shown has a simplified set of components. In this configuration, a flexible or rigid/flex printed circuit board (PCBA) 2320 may be used so that it may flex with a flexible housing 2020 with interior walls (for example, an upper and lower wall) and adhesive patch 2200. The lower major wall is disposed on top of the adhesive patch, and the upper major wall is above the lower major wall, similar to other sensor configurations shown herein. Example materials for the flexible housing include silicone and polyurethane, but other suitable materials may be used. In alternate configurations, the PCBA and or the housing may be rigid, although the flexibility of these components may lend themselves to increased comfort by the user. A sensor 2012 is attached to the PCBA 2320 and its end extends through the PCBA into the user's body. A molded support 2325 is provided to support needle insertion and to capture and hold the sensor. A battery 2300 is held in place by battery clip 2302. Alternately, the battery may be affixed to the PCBA or contained in the housing 2020 in other manners described herein. FIG. 19 shows a side profile of the configuration shown in FIGS. 17 and 18, with a needle insertion tool 2400, including a needle 2410 attached for insertion of the sensor into the body of a user. This small size sensing device allows for added comfort for a user, along with reduced profile under clothing.

The simplification of the number of components and their configuration within the housing allows for the reduced size of the sensor, which allows for increased comfort to the user. The molded support 2325 supports the needle and, when centered in the housing, allows the sensing device to maintain flexibility along its longer axis.

The molded support may be a T-shaped support with a cross arm extending transversely across the housing/case. The T-shape of the molded support 2325 allows for stability of the flexible sensing device while holding the sensor 2012 securely in place. The first end of the housing has the battery and battery clip, with a central section having the molded support. The molded support includes a stem that extends towards the second end of the housing, where it holds the end of sensor with the sensor contact pads. The stem has a guide channel for the sensor from the opening in the lower major wall. The T-shaped support may extend from the lower major wall to the upper major wall at the intersection of the cross arm and stem. Additional components may be housed inside the housing near the second end of the housing. Sensor electronics (not shown), for example, maybe housed in the second end of the housing, including electronics to determine whether the sensor is sensing an analyte level that is above, below, or within a desired range. Lights (not shown) such as LED lights may be included in the exterior of the housing, and may be used to indicate analyte levels. As an alternative, the housing may be at least partially translucent with lights inside the housing. The lights can be seen through the at least partially translucent housing to indicate glucose levels. Other indicators of analyte levels that are out of the normal range may be used. For example, the sensing device may be configured to vibrate and/or sound an audible alert when the analyte level is outside of a normal range.

Figure 20:
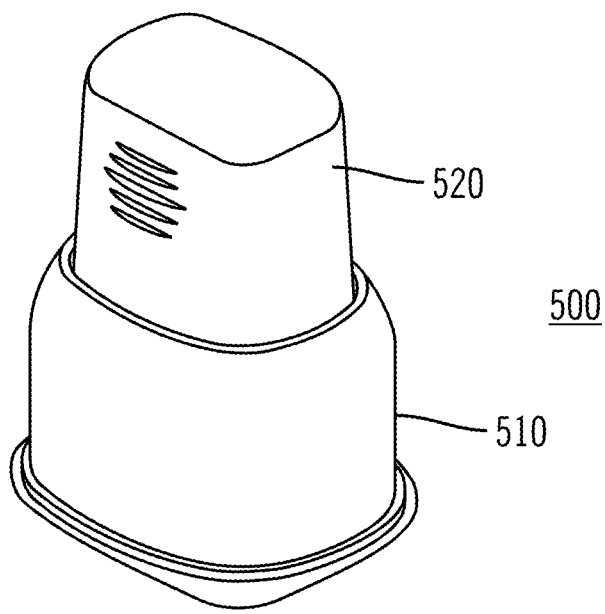
FIG. 20 illustrates a perspective view of an insertion tool.

The sensing device 100 disclosed herein according to one or more embodiments may be placed onto a user using a disposable insertion tool. Insertion tools that interact with the presently disclosed sensing device can work similarly to previously disclosed insertion tools, for example as disclosed in U.S. Pat. Nos. 5,851,197, 6,093,172, and 6,293,925, which are herein incorporated by reference. In particular, it is possible to provide an insertion tool that is shaped to hold the sensing device disclosed herein, pre-loaded with a sensing device. As shown in FIG. 20, the insertion tool 500 includes a sensor holder 510, which is configured to hold the sensing device until it is placed onto a user's skin, with its sensor inserted into the skin. The insertion tool 500 also includes a retractable push button 520. When a user wishes to place the sensing device onto the skin, with sensor inserted and ready for use, the user places the disposable insertion tool 500 with preloaded sensing device onto the skin. The push button 520 is depressed fully so that the internal needle (not shown) inserts the sensor into the skin of the user. The needle is then automatically retracted when the push button 520 is released. In various embodiments, the sensing device remains on the user's skin adhered to the skin by use of an adhesive patch, with the sensor inside the user's body. The battery pull tab may then be removed to initiate the sensing device. The insertion tool 500 with its needle inside can then be disposed of. After the sensing device is placed and the battery pull tab is removed, a wireless transmitter inside of the sensing device begins pairing to an infusion pump, glucose monitor or other receiver. Examples of infusion pumps and glucose monitors that interact with wireless receivers are shown, for example, in U.S. Pat. Nos. 7,942,844; 8,073,008; and 8,344,847, which are herein incorporated by reference.

A configuration of an insertion tool is shown in FIGS. 23A-23D. The insertion tool 1500 includes an external lock collar 1510, which is configured to house the components of the insertion tool. The push type plunger 1520 is housed in the lock collar 1510. The insertion tool 1500 holds the sensing device until it is placed onto a user's skin. When a user wishes to place the sensing device onto the skin, with sensor inserted and ready for use, the user places the disposable insertion tool 1500 with preloaded sensing device onto the skin. The plunger 1520 is depressed fully so that the internal needle (not shown) inserts the sensor through the skin of the user. The needle is then automatically retracted when the plunger 1520 is released. This leaves the sensing device adhered to the skin with the sensor inside the user's body. The adhesion may be provided by use of an adhesive patch.

The insertion tool 1500 further includes a visual indicator of locked/unlocked status. For example, an arrow 1512, which extends slightly out of the surface of the plunger 1520, is shown in the configuration in FIG. 23A. The arrow 1512 may alternatively be another shape that allows for visual indication of locked/unlocked status. A cutout 1513 is made in the external lock collar. In the configuration shown in FIG. 23A, when the arrow 1512 is not lined up with the cutout 1513, the insertion tool is locked, preventing the plunger 1520 from being depressed.

A cover 1580 covers the bottom of the insertion tool such that a sensing device inside the insertion tool, as well as any internal components, are covered before use of the insertion tool. The cover also prevents the user from being able to unlock and fire the insertion tool until after the cover is removed. The cover adheres to both the frame and to the lock collar, effectively attaching (e.g., gluing) the lock collar in place so that it cannot be rotated. With the cover in place, any adhesive patch on the sensing device will not need an additional liner to cover the adhesive. When the cover 1580 is removed, the adhesive patch is ready to be attached to the skin of the patient.

Figure 23A:
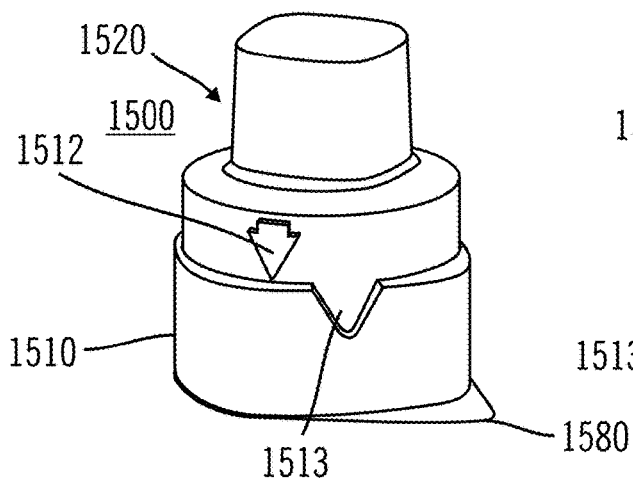
FIGS. 23A-23D illustrate perspective views of an insertion tool.
Figure 23B:
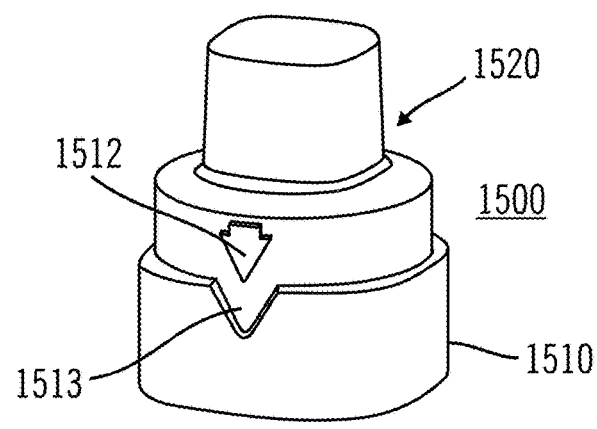
Figure 23C:
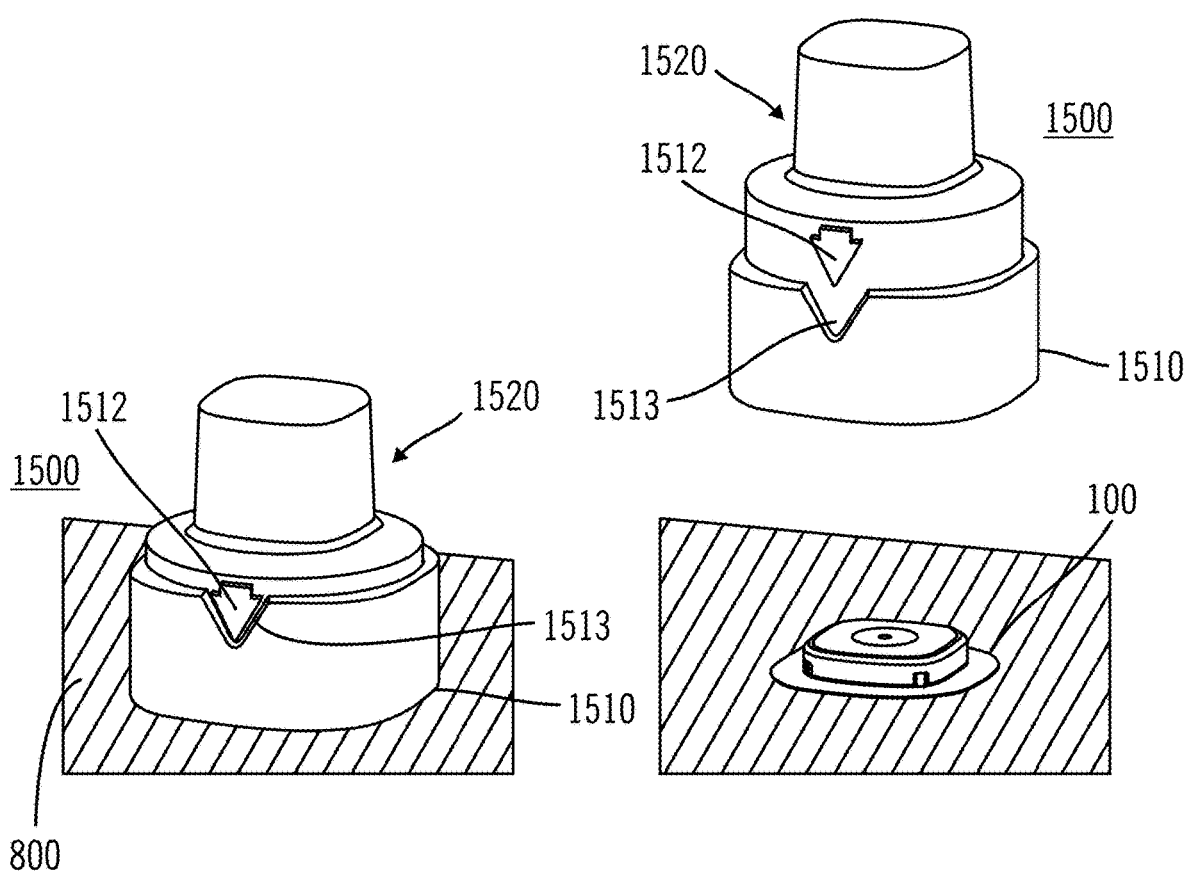
Figure 23D:
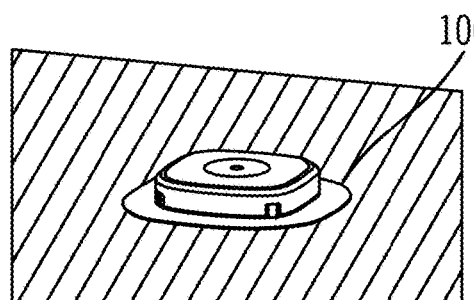

In FIG. 23B, the cover has been removed, and the plunger 1520 has been turned so that the arrow 1512 lines up with the cutout 1513. At this point, the insertion tool has been unlocked, such that the plunger 1520 may be depressed. The insertion tool 1500 containing a sensing device can then be placed on the skin 800 of a user, as shown in FIG. 23C. The plunger 1520 is depressed, whereby the arrow 1512 fits into the cutout 1513, and the insertion needle (not shown) inserts the sensor (not shown) through the skin of the user. Once the sensor is properly inserted into the user, the sensing device 100 can be released from the insertion tool 1500, as shown in FIG. 23D. The needle and other components are retracted into the insertion tool for safety.

Figure 26:
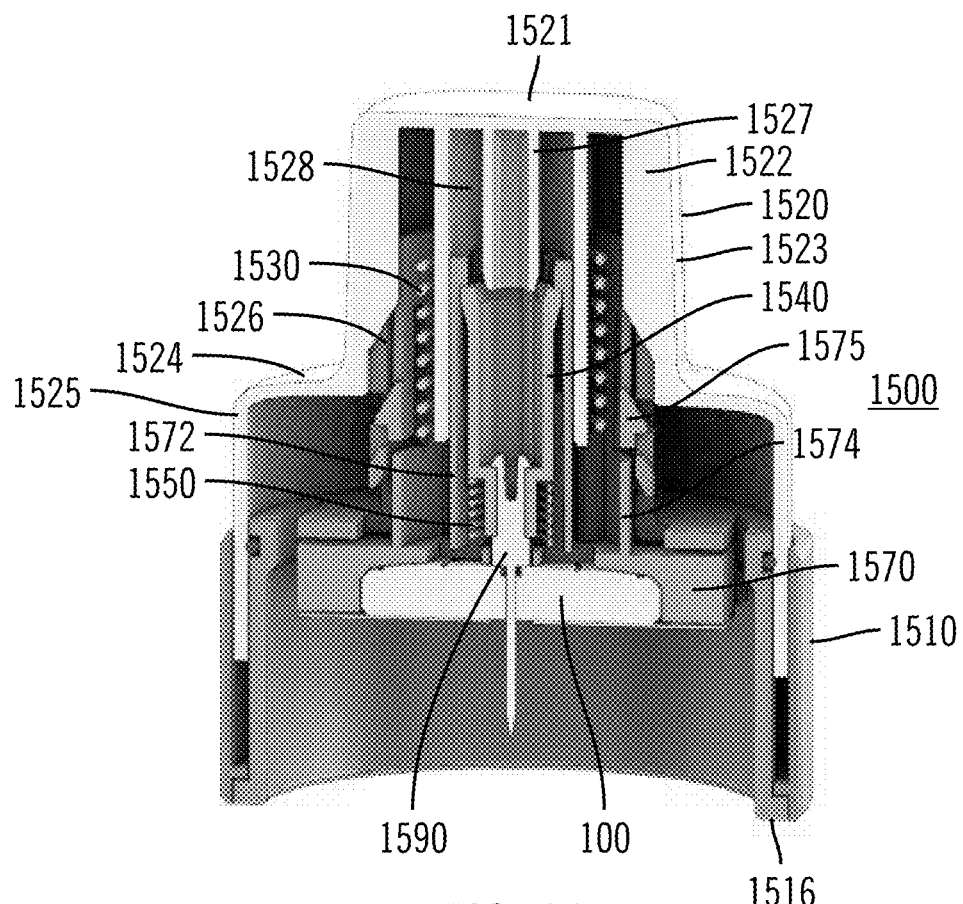
FIG. 26 illustrates a side cutaway view of an insertion tool.

The internal structure of the insertion tool 1500 can be seen in FIG. 26, which shows the tool in its pre-fired and pre-cocked state. This state corresponds to FIG. 23B described above. The plunger 1520 comprises a push button head 1522 with a flat top 1521 and a cylindrical side wall 1523. The side wall 1523 can have a shallow taper to make it easier to manufacture. The side wall merges via a shoulder 1524 to a wider diameter dependent skirt portion 1525. This skirt portion carries on its outer surface the arrow 1512 described with reference to FIGS. 23A-23D. The inner surface of the cylindrical side wall 1523 of the push button head 1522 has a cam surface sloping radially inwardly with increasing height inside the push button head 1522. Dependent from the flat top 1521 and co-axial are an inner cylindrical wall 1527 and an outer cylindrical wall 1528. The dependent skirt portion passes into an annular gap formed between an inner cylindrical surface of lock collar 1510 and an outer cylindrical surface of an inverted cup-shaped frame 1516.

Figure 24:
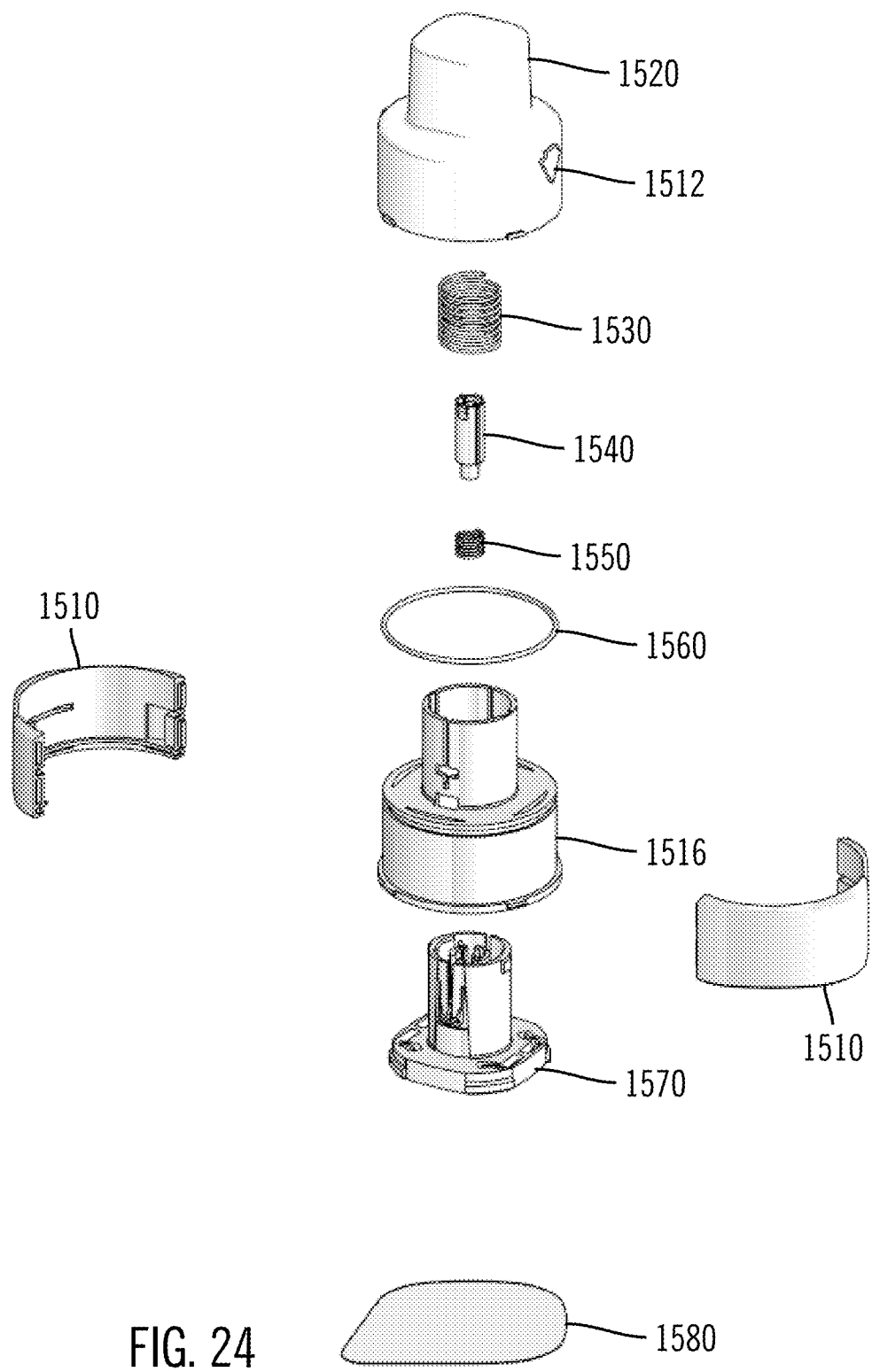
FIG. 24 illustrates an exploded view of an insertion tool.

An expanded view of the insertion tool 1500 of FIG. 26 is shown in FIG. 24. The plunger 1520 is shown with arrow 1512. An insertion spring 1530 which is contained in another gap formed between the outer cylindrical wall 1528 and the side wall 1523 of the plunger push button head 1522 compresses when the plunger 1520 is depressed storing energy for the firing of the tool 1500. A needle hub carrier 1540 is adapted to carry the needle hub (not shown), which holds the insertion needle used to insert the sensor of the sensing device into a patient. A retraction spring 1550 is included for retracting the needle hub into the body of the insertion tool after insertion of the sensor. The frame 1516 supports the various components and provides contact with the patient's skin during use. The lock collar 1510 is shown in 2 parts and fits around the frame 1516. An O-ring 1560 seals between the frame 1516 and an inner surface of the plunger skirt portion 1525. A striker 1570, which acts as a sensing device holder and is adapted to hold a sensing device, fits into the frame 1516. The striker has locking structures for engaging both the frame 1516 and the needle hub carrier 1540. The cover 1580 covers the bottom of the insertion tool before use.

Figure 25:
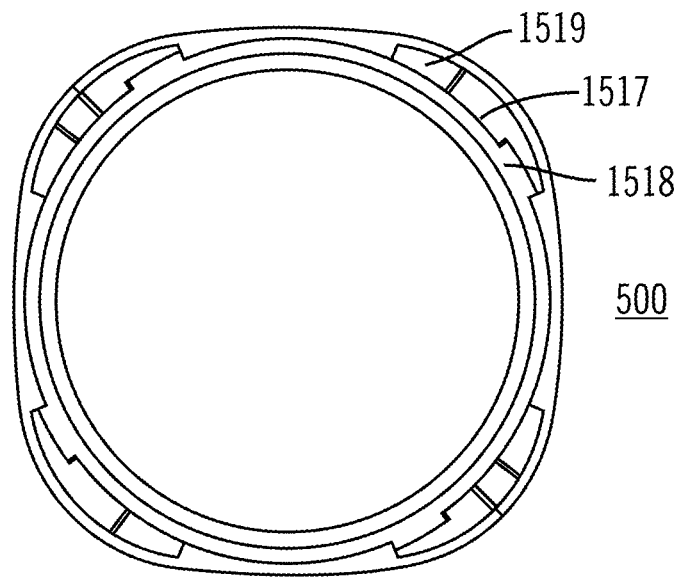
FIG. 25 illustrates a cutaway view of an insertion tool.

The insertion tool may include an unlocking mechanism to prevent the insertion tool from firing during storage. As discussed above, with respect to FIGS. 23A-23D, the insertion tool may include a visual indicator of locked/unlocked status. When the visual indicators line up, it will indicate that the insertion tool is unlocked. FIG. 25 shows a cutaway of the insertion tool showing tabs 1518 which can line up with recesses 1519 to unlock the insertion tool. Otherwise, they are blocked by shelf 1517 such that the insertion tool is locked and cannot fire. In the illustrated arrangement radially outwardly extending tabs 1518 on the plunger 1520 prevent it from being moved axially with respect to the lock collar 1510 unless the tabs 1518 align with recesses in the lock collar 1510. It is also possible for the tabs to be on the lock collar and the recesses on the plunger. This helps prevent accidental firing in storage due to rough handling.

As shown in FIG. 26, the needle hub 1590 is contained inside the needle hub carrier 1540. In another configuration, the needle hub and needle carrier may be together in one piece. Before insertion, the plunger 1520 is in an extended position and the needle 410 is held inside the insertion tool, as is the sensor 100. The sensor is held within a cavity in the underside of the striker 1570. The striker itself has two upstanding co-axial cylindrical walls. The inner wall has hooks on its upper rim which has outwardly facing barbs 1575 which engage holes in an upstanding holding structure on the frame. This locks the striker to the frame, preventing axial movement of the striker 1570. As the plunger 1520 is depressed, it compresses the insertion spring 1530 priming/cocking it ready for firing. At the end of its travel the cam surfaces 1526 on the inner walls of the plunger engage the barbs 1575 on the striker outer upstanding wall 1574, unhooking them from their corresponding holes in the upstanding holding structure on the frame. The striker 1570 then is free to travel downwards propelled by the newly cocked spring. It carries with it the sensor 100, needle 410, needle hub 1590 and carrier 1540. Vents in the striker allow air to exchange across the striker surface during travel. The interior of the insertion tool is shaped to guide straight insertion of the needle into the body of the user. Guidance of the travel of the striker 1570 is provided by the inner upstanding wall 1572 on the striker. As well as inwardly facing hooks which retain the needle hub carrier 1540, this wall has a smooth outer surface which runs against the outer dependent co-axial cylindrical wall 1528 within the plunger push button head 1522.

Figure 27:
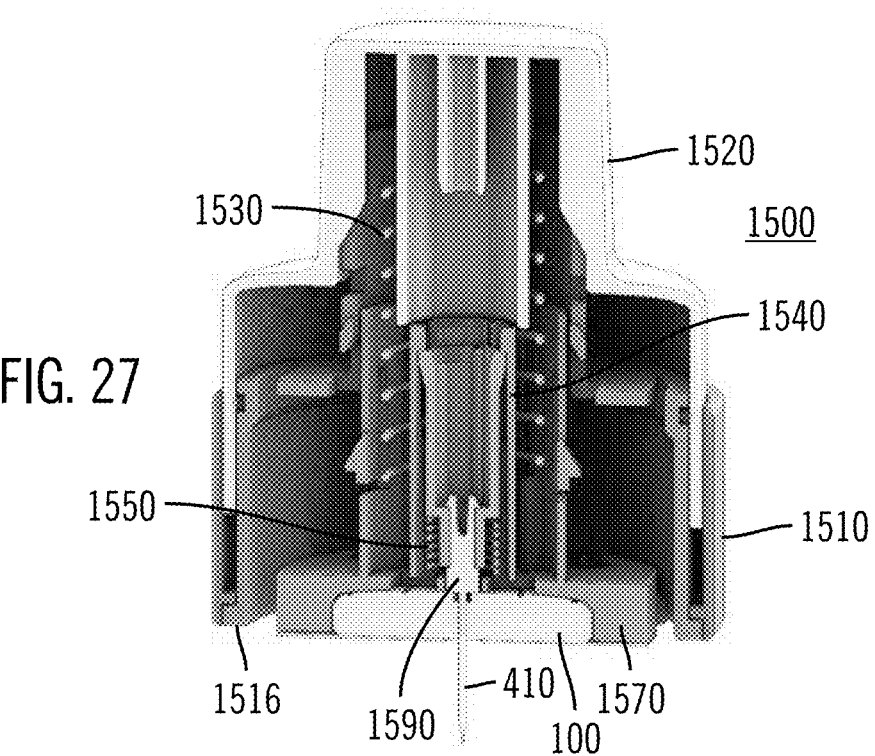
FIG. 27 illustrates a side cutaway view of an insertion tool.
Figure 28:
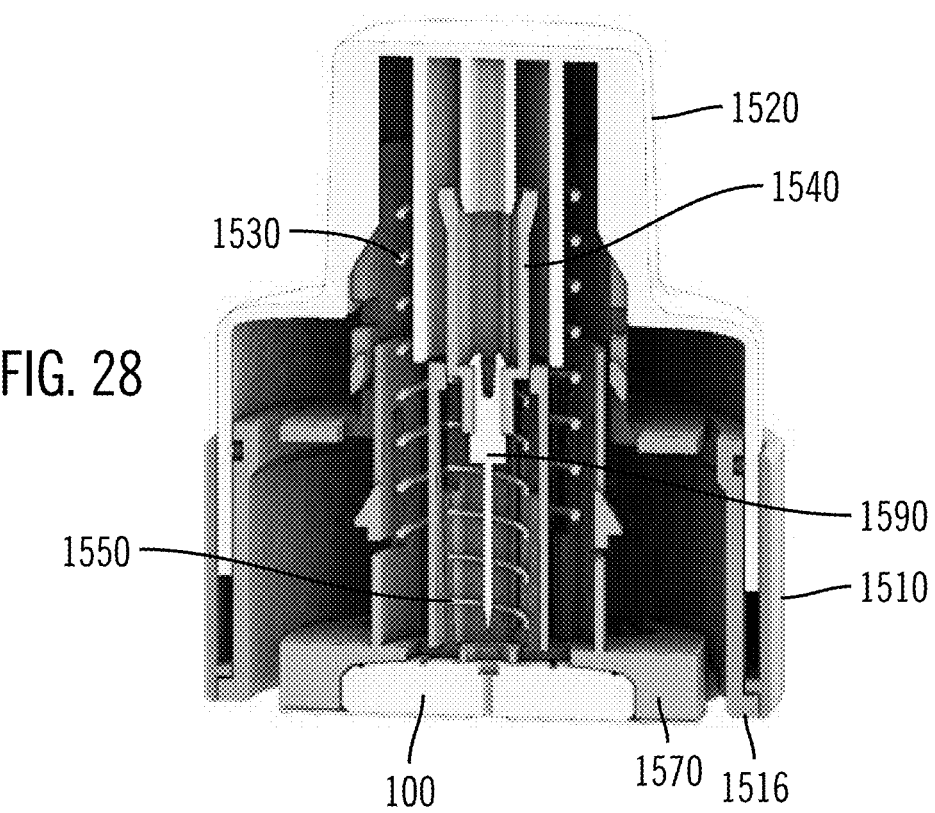
FIG. 28 illustrates a side cutaway view of an insertion tool.

To fire the tool the user places the tool on the skin with the lower rim of the frame 1516 against the skin, then with the angular orientation correct, the user presses on the plunger 1520 holding it by the push button head 1522. The plunger 1520 moves downwards. As the striker 1570 is locked to the frame via the barbs 1575 engaging holes in the upstanding portion of the frame, it remains stationary, at least initially. The downward movement of the plunger, however compresses the spring 1530. Prior to this movement the spring can be in a relaxed state. The downward movement of the plunger continues until the cam 1526 on the inner wall of the push button head 1523 of the plunger press against the barbs 1575 on the striker 1570. The plunger has now reached its firing position, and further downward force unlocks the barbs from the holes in the frame 1516 allowing the striker to travel downwards under the force of the spring 1530. As the force applied to the plunger during the cocking and firing operation is applied with the tool against the skin this force also holds the tool in place. As it includes the force to release the lock the force to fire the insertion tool is greater than the force exerted by the insertion spring 1530 against the insertion site at the end of insertion. The firing mechanism guarantees that the insertion tool is held against the insertion site with enough force to fully insert the needle 410 and adhere the patch of the sensing device 100 to the skin. The sensor base sits below the bottom of the striker 1570, which travels beyond the mouth of the frame 1516, as shown in FIG. 27. The insertion spring load is distributed primarily over the sensor base bottom surface. The needle retraction mechanism actuates automatically as the user lifts the insertion tool from the insertion site. This occurs because, when the striker is at its extended position at the mouth of the frame any upward movement of the plunger causes the upstanding wall 1572 on the striker to escape the confines of the outer dependent cylindrical wall 1528 of the plunger. As soon as that happens the hooks on the striker release the needle carrier 1540, causing the needle to be pulled out of the sensor 100. This procedure is aided by the insertion spring 1530 which pushes the plunger 1520 back towards to its original position. The plunger travel releases the needle hub 1590, triggering retraction of the needle 410. The mechanism guarantees that full insertion occurs at the insertion site, along with the retraction sequence. The insertion tool cannot retract the needle until after insertion, and the user cannot remove the insertion tool from the site without actuating the needle retraction. FIG. 28 shows a cutaway of the insertion tool after the needle hub 1590 has been retracted back into the insertion tool.

Figure 29:
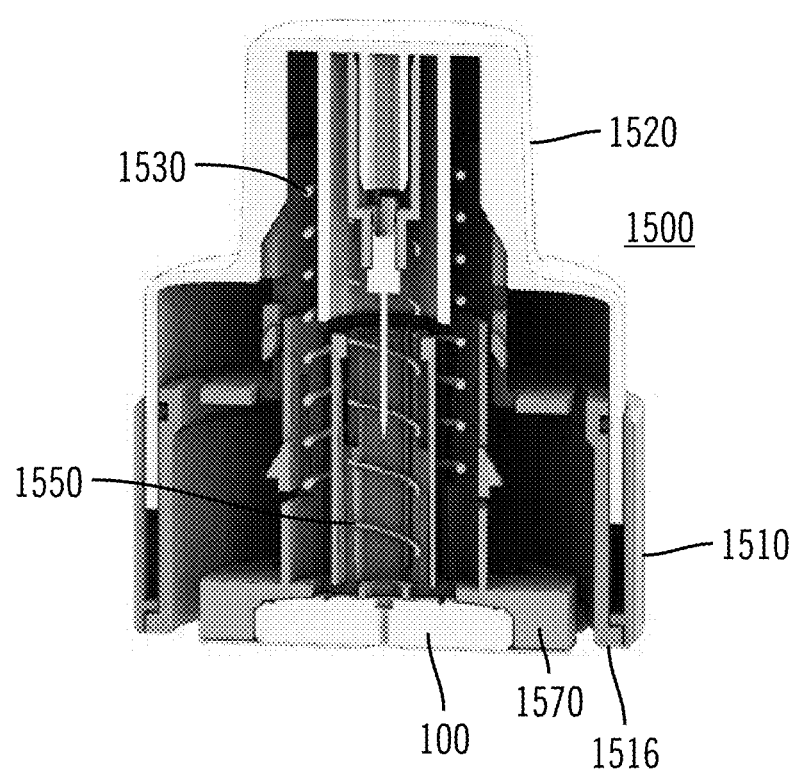
FIG. 29 illustrates a side cutaway view of an insertion tool.

As further shown in FIG. 29, as the needle hub retracts, cams (not shown) on the plunger rotate the needle hub, for example by about 60 degrees. The retraction spring 1550 keeps the needle hub carrier 1540 held against the plunger 1520, in the rotated position. In the rotated position, guide rails on the bottom of the needle hub carrier 1540 interfere with the top of the striker 1570 preventing the needle carrier from descending into the striker 1570 even if a user presses again on the plunger. The needle hub carrier 1540 can even effectively become a wedge between the plunger 1520 and the striker 1570, preventing the user from depressing the plunger and striker at the same time, which would re-expose the needle tip. The user is also prevented from cocking and firing the insertion tool again, which could break the insertion tool and eject the needle. Because the insertion tool automatically retracts the needle hub into its interior, this embodiment reduces the number of steps from prior art insertion tools, which generally require that the user manually retract the needle into the insertion tool after use.

Figure 30A:
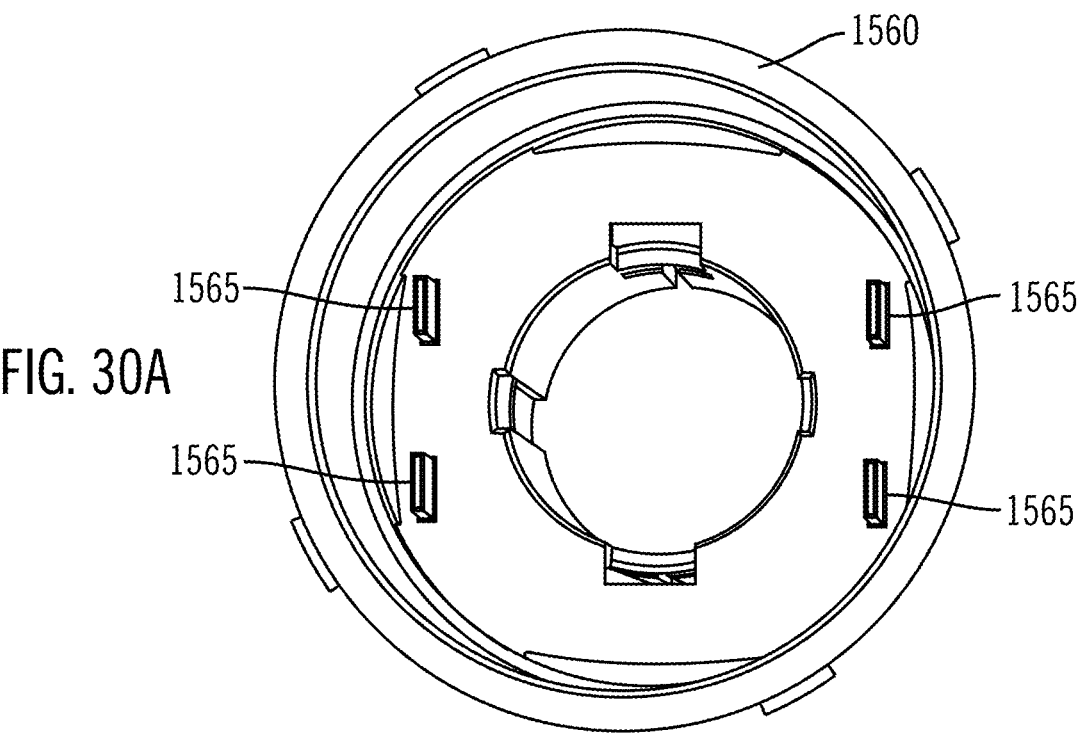
FIGS. 30A-30C illustrate bottom views of a portion of an insertion tool.
Figure 30B:
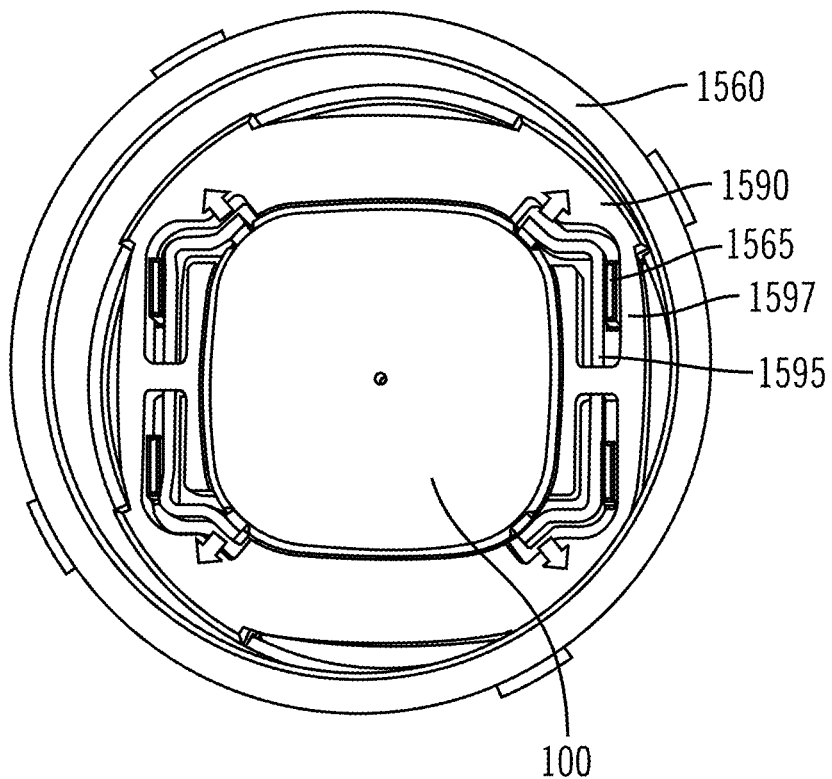
Figure 30C:
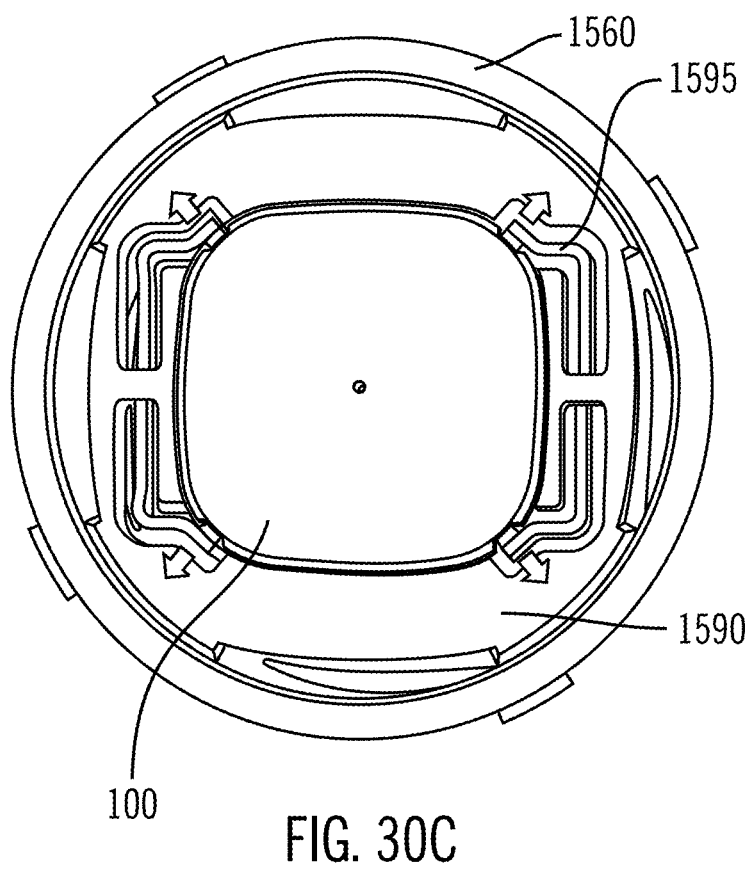

The sensor may be released from the insertion tool through a sensor release mechanism shown in FIGS. 30A, 30B, and 30C. FIG. 30A shows a frame 1560 from below and by itself. The frame includes four frame ribs 1565 on its inner surface, extending toward the bottom of the frame. FIG. 30B shows the frame 1560 from below, with the striker 1590 sitting inside the frame. In the configuration shown, before the insertion tool is used, the sensor 100 is held inside the striker 1590 by snap arms 1595 at four corners. The four frame ribs 1565 fit between the four snap arms 1595 and the side walls 1597 of the striker 1590. When the striker is in this pre-firing position, the frame ribs 1565 on the frame 1560 effectively shorten the snap arm length, increasing the force required to deflect them and locking the sensor 100 in place. Thus, the sensor will not dislodge from the striker if the insertion tool is dropped onto a hard surface before use. After the insertion tool has been fired, as shown in FIG. 30C, the frame ribs (not shown) on the frame 1560 cannot reach the striker and thus no longer interfere with the snap arms 1595, decreasing the deflection force. In this configuration, the snap arms 1595 can flex along their entire length. This greatly reduces the force required to pull the sensor out of the striker, allowing the sensor to automatically release when the insertion tool is lifted away from the site and making it more comfortable on the skin when the insertion tool is lifted away from the site.

When the sensing device is nearing its end of life, it may give a warning to indicate that it is nearly time to replace it. For example, an audio alarm, vibration, etc. may be given as a warning. The user can then remove the current sensing device, insert a new sensing device, begin its start up, and pair it to a pump or other receiver. When the new sensor start up is complete, the readings will begin from the new sensor, disabling the old sensor and signaling the user to remove the old sensor. In various embodiments, the user will insert a new sensor prior to the old sensor, allowing continuous monitoring of the sensed analyte. However, it is possible to remove the old sensor prior to inserting a new one, which would result in some missed time sensing the analyte.

Among the advantages of the presently disclosed sensing device according to various embodiments, is the ability to reduce downtime between sensors. Currently, when using reusable sensor electronics, the user disconnects the sensor electronics from the disposable sensor, places a new sensor into the body, and reconnects the sensor electronics. Only when the sensor electronics are connected to the new sensor can monitoring begin. In addition, sensing and therapy must be stopped to recharge the sensor electronics. With an integrated device, the user no longer needs to recharge the transmitter, so no time is lost for recharging. Also, the new sensor may be initialized while the old sensor is still reading and transmitting. It is estimated that using the integrated sensor can eliminate at least 60 minutes of charge time and 90 minutes of start up time.

Integrating the transmitter and the sensor eliminates several steps from starting a sensor. It eliminates transmitter recharging, transmitter connection and disconnection to the sensor and transmitter cleaning, which is necessary when using a long-term sensor electronics/transmitter device. The integration of the transmitter and sensor further eliminates the need for a transmitter charger and the need for a test/charging plug, which is used to connect to reusable sensor electronics/transmitters during cleaning (when the sensor electronics are separated from the sensor).

The integration of the transmitter and the sensor further reduces risk to the user from trying continuous glucose monitoring. With an integrated, disposable system, there is no need for a prospective user to buy an expensive start up kit (transmitter, charger, insertion tool, and cleaning plug) before trying the sensor. This greatly lowers the risk of trying continuous glucose monitoring for the first time, or of switching among different competitors' continuous glucose monitoring systems. In addition, it reduces the number of components necessary to carry around with an analyte monitoring device.

Another advantage of integrating the transmitter and the sensor is the elimination of mismatching of sensors and transmitters. With separate sensor electronics/transmitter and sensors, there is danger of mismatching the sensors and transmitters, which can result in incorrect readings. Currently, mechanical lockouts are used to ensure that transmitters cannot be connected to incompatible sensors. With a disposable, integrated device, it is no longer possible to pair incompatible sensors to transmitters. Without the concern of incompatible devices, it is possible to release updated sensors more easily and more frequently.

While the sensing device of the present disclosure according to one or more embodiments is not reusable, it is potentially recyclable in that the unit could be sent back to the manufacturer for reprocessing and reuse of any number of components.

The sensing device described herein transmits data to a separate monitor, which may be of the type suitable for determining glucose levels in the body and/or body fluids of the user and may be used in conjunction with automated or semi-automated medication infusion pumps of the external or implantable types as described in U.S. Pat. Nos. 4,562,751, 4,678,408, 4,685,903, and 4,573,994, which are herein incorporated by reference, to deliver insulin to a diabetic patient. However, it will be recognized that the integrated sensor/transmitter or sensing device according to one or more embodiments may be used in arrangements to determine the levels of other agents, characteristics or compositions, such as hormones, cholesterol, medication concentrations, pH, oxygen saturation, viral loads (e.g., HIV), or the like. The sensing device may also include the capability to be programmed or calibrated using data received by the sensor electronics, or may be calibrated at the monitor device. The sensing device is primarily adapted for use in subcutaneous human tissue. However, it may be placed in other types of tissue, such as muscle, lymph, organ tissue, veins, arteries or the like, and be used in animal tissue. It will be understood that the term "patient" can be broadly construed to encompass humans and other animals, and that the term "blood" encompasses patient blood and other extracellular patient fluids. Embodiments may provide sensor readings on an intermittent or continuous basis.

According to one or more embodiments, the sensing device described herein uses an electrode-type sensor. However, the sensing device may use other types of sensors, such as chemical based, optical based or the like. It should be noted that in various embodiments, sensors can be electrochemical sensors or optical sensors including fluorescent sensors. Examples of optical sensors are described in U.S. Pat. Nos. 6,011,984, 7,228,159, 7,751,863, 8,467,843, and 9,399,076, which are herein incorporated by reference. Furthermore, in various embodiments, the sensors may be of a type that is used on the external surface of the skin or placed below the skin layer or the user. Certain surface mounted sensors could utilize the interstitial fluid harvested from underneath the skin.

The sensing device described herein according to one or more embodiments may be used in conjunction with other continuous analyte (e.g., glucose) monitoring systems. One system that can be used in conjunction with the sensing device described herein according to various embodiments, other continuous monitoring systems or more intermittent monitoring systems (such as finger stick blood glucose tests) or on its own is a simple continuous analyte monitoring device with visual indicators. Visual indicators are useful for behavior modification of pre and type 2 type diabetic patients.

A simple continuous glucose monitoring (CGM) device is provided with only visual indicators for behavior modification of pre and type 2 diabetic patients. This simple device allows for monitoring of blood glucose without the need for a handheld reader or other communication device such as a smartphone, tablet, or other such device. In other configurations, data obtained by the simple CGM device can be stored and downloaded to another device such as a smartphone, tablet, or the like.

Figure 21:
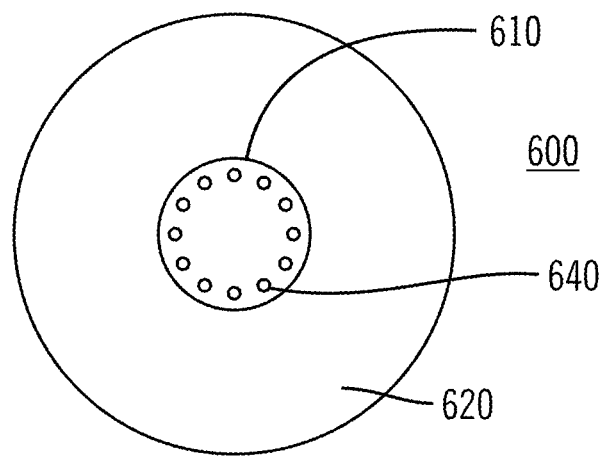
FIG. 21 illustrates a top view of a sensing device.

FIG. 21 shows one embodiment of a visual analyte sensor 600. In this embodiment, the visual analyte sensor 600 includes an adhesive patch 620 to adhere the sensor to the skin. The sensor housing 610 includes one or more indicators including one or more visual indicators such as LED lights 640. In various configurations, the visual indicators may be of any shape, size or color, and may be any appropriate display such as the LED lights 640, LCDs, OLEDs, fluorescent lights, E-ink displays, or the like. In some configurations, numerous indicators such as lights or LEDs can make up a row or ring (or any other appropriate shape) of lights or LEDs to indicate a sliding scale. For example, the sliding scale may indicate the glucose level. In an example where the lights or LEDs make up a bar, a green light may be at the center of the bar, and as the glucose level shifts up or down, the LED lights away from the center LED and may change into other colors.

In one configuration, the LED lights may be capable of multiple colors that change when a normal blood glucose range changes to a high blood glucose range. For example, a green color could indicate a normal blood glucose range and a red color could indicate a high blood glucose range.

The lights may be configured such that quick blinks indicate a fast rise or fall of glucose trends. For example, quick blinking red could indicate a fast drop in glucose, and quick blinking green could indicate a fast rise in glucose. LED colors could include various colors to indicate points in a range from hyperglycemic to hypoglycemic level. For example, red could indicate hypoglycemia and yellow could indicate hyperglycemia. Blinking lights, and the rate of the blink could signify particular glucose levels. For example, fast blinking lights could indicate high levels of blood glucose and slow blinking lights could indicate low levels of blood glucose. In addition, blinking or steady lights could describe a status of the sensor readiness or reliability. Numerous LEDs can make up a row or ring (or any other appropriate shape) of LEDs to indicate a sliding scale. This sliding scale could show where the glucose level is. Colors could be used in such a sliding scale. For example, in one configuration, where the lights or LEDs make up a bar, a green light may be at the center of the bar, and as the glucose level shifts up or down, the LED lights away from the center one and may change into other colors such as yellow for nearing high/low levels and red for reaching high/low levels.

Figure 22:
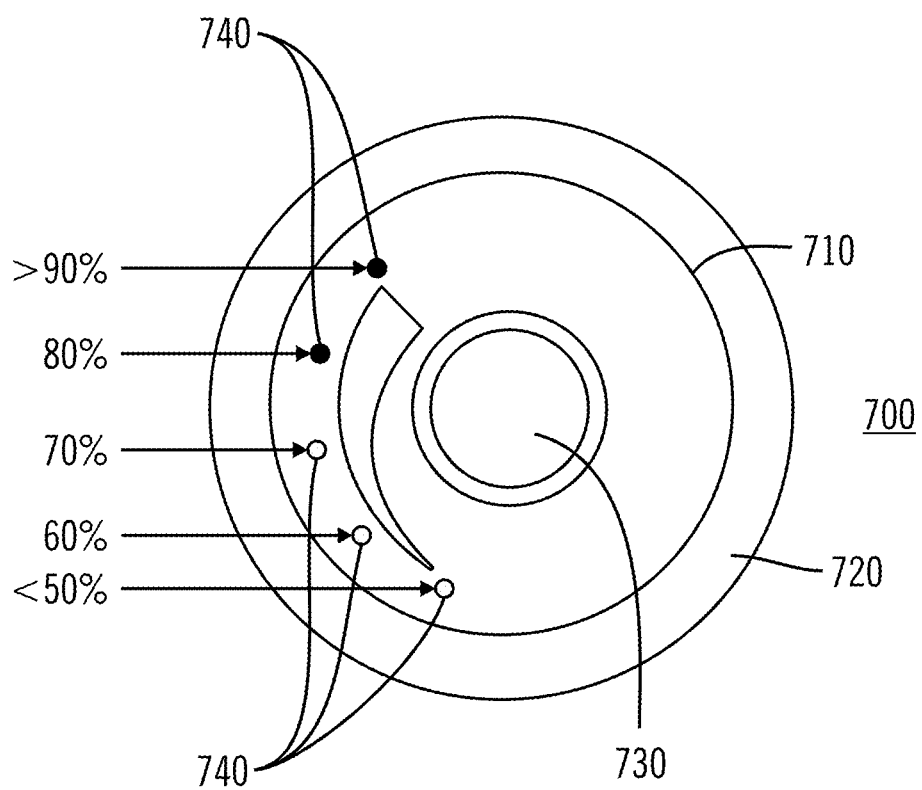
FIG. 22 illustrates a top view of a sensing device.

In a different arrangement, lights could be used to indicate the percent time in a target (i.e., normal) blood glucose range. One example of this is shown in FIG. 22. A visual analyte sensor 700 is on an adhesive patch 720. A central light 730 may be used to indicate whether the blood glucose level is within normal or high levels. A series of lights 740 may indicate what percentage of the time the sensor was worn that the blood glucose was within normal range. For example, the lights shown in FIG. 22 could indicate 50%, 60%, 70%, 80%, and >90%. Other useful sets of numbers or configurations could be used. The partial circle shown in FIG. 22 has some usefulness in that it is easy to view, at a quick glance, how well the user's blood glucose levels have been doing. However, this configuration is not intended to limit other potential arrangements (full circle, square, other array, etc.).

In various configurations the visual analyte sensor can include an alarm such as an audio alarm, vibration, etc. to indicate that an abnormal blood glucose level (not in target) is being approached or that it has been reached.

The visual analyte sensor according to an embodiment includes a minimally invasive sensor, such as one with microneedles to minimize pain. Examples of using microneedles to sense blood analytes can be found, for example in PCT Application No. PCT/US1999/029925, WO2000035530, which is herein incorporated by reference. Alternatively, a needle inserted sensor, such as the one described herein or known in the art can be used.

In one or more embodiments, the entire visual analyte sensor is flexible and can conform to the skin. To achieve this flexibility, the sensor housing may be made out of a flexible material such as silicone or polyurethane. Other flexible materials that can successfully house and protect the electronics of the sensing device may also be used. Some examples include silicon, fabric, plastic (e.g., polycarbonate or ABS), or other flexible polymers. In further embodiments, the circuit board for the electronic components of the sensing device is also flexible.

One use of a visual analyte sensor as described could be as a self-screening device. For example, a self-screening, disposable, calibration-free retrospective CGM device to be sold over-the-counter. This type of device could be used by a patient who is an undiagnosed pre-diabetic or type 2 diabetic who may have been indicated in an annual check-up about possible diabetes or may suspect diabetes themselves based on symptoms. A patient could buy the sensor, install it on the body and, after a period of time (e.g., 1-7 days), the visual indicators such as LED lights would indicate whether they might be at risk for diabetes. It is possible that there could be no indicators during the wear, but that they would only occur at the end of the pre-determined wear time. The patient would then be directed for further checkup with a doctor. For example, the device shown in FIG. 21 could be used for this type of self-screening device. If the lights are configured to be red or green (or any other appropriate color), the device could be set up for the lights to be red or green at the end of the predesignated time period. Because the device is a one time, disposable device, patients would see the value in buying such a device before going through the hassle of doctor appointments.

Another use of the visual analyte sensor would be for self-monitoring, calibration free, real time monitoring by a device sold over the counter. In self-monitoring, the device would have a real time blood glucose display. The devices in FIG. 21 and FIG. 22 are sample embodiments of visual analyte sensors that could be used for self-monitoring. The patient in this case would be a type 2 diabetic who is on a diet and exercise and/or oral medication regimen. The device would be used for behavior modification for improved quality of life through diet and exercise. This may not require the need to know the exact blood glucose values as the patient is not treating themselves with insulin or other medication that needs to be carefully balanced. Instead, this patient requires a device that allows other modifications, such as diet and exercise. In the case of the device shown in FIG. 22, the device has a few more lights to show the time in a target range during the wear life or certain periods of time (such as the last 24 hours). The motivation for the patient is to maximize the percent of time in target values to stay healthy and reduce long term complications.

In further aspects, indicators as described herein such as the LED indicators shown in FIGS. 21 and 22 and discussed above, are combined with the other sensor configurations discussed herein. For example, either sensor configuration shown in FIGS. 4-9 or in FIGS. 11-16B could also include indicators including lights such as LED lights in the housing. The LED lights could be as shown in FIG. 21 or FIG. 22 or in another configuration desired such that analyte values can be indicated to a user (either current or over a predetermined amount of time).

Embodiments herein may be used with various types of monitoring systems, for example, with a sensor and transmitter product that includes a reusable transmitter, as described, for example, in U.S. Pat. No. 10,631,787, the contents of which are hereby incorporated by reference in their entirety.

The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. An apparatus for placing a medical device on a surface of a skin of a patient and inserting a filament extending from the medical device into the skin of the patient, comprising:

a frame having a mouth for positioning against the skin during placement of the medical device, and an internal cavity for retention of the medical device prior to placement;

the medical device having a surface adapted to be held against the skin of the patient and having the filament extending therefrom;

a retractable needle extending through the medical device and carrying the filament;

a striker holding the medical device and being axially movable within the frame from a first retracted position within the frame to a second position in which the surface of the medical device is presented at the mouth of the frame;

a driver configured to urge the striker towards the second position;

a releasable striker lock holding the striker in the first retracted position; and a plunger axially movable with respect to the frame in a direction towards the mouth, from a rest position to a firing position, the apparatus having a mechanism configured to release the releasable striker lock when the plunger reaches the firing position, allowing the striker to move from the first retracted position to the second position.

2. The apparatus according to claim 1, wherein the striker includes resilient snap arms engaging a perimeter of the medical device to releasably hold the medical device in the striker; and wherein the frame includes ribs which contact the resilient snap arms when the striker is in the first retracted position to increase the force needed to release the medical device from the striker.

3. The apparatus according to claim 2, wherein the ribs are fixed on the frame and extend longitudinally into the striker, touching the resilient snap arms when the striker is in the first retracted position.

4. The apparatus according to claim 2, wherein the medical device is substantially rectangular and is held in the striker by four of the resilient snap arms, one acting on each corner of the medical device.

5. The apparatus according to claim 1, wherein the driver is a spring longitudinally extending between the striker and the plunger, such as to compress as the plunger is moved from the rest position to the firing position.

6. The apparatus according to claim 1, wherein the releasable striker lock comprises an engagement between upstanding extensions on the frame and the striker, and wherein the plunger includes a cam surface to dislodge the engagement.

7. The apparatus according to claim 1, further including:
a retractor exerting a force on the retractable needle in the direction to pull the retractable needle out of the medical device;
a releasable retractor lock preventing the retractor from pulling the retractable needle out of the medical device; and
a retractor lock release mechanism configured to release when the striker is in the second position and the plunger moves away from the firing position.

8. The apparatus according to claim 7, wherein the retractor is a spring acting on a needle hub attached to the proximal end of the retractable needle.

9. The apparatus according to claim 1, wherein the plunger comprises a push button head adapted to be gripped by a user merging via a shoulder portion to a wider diameter dependent skirt portion; and the apparatus further includes an external collar surrounding the frame and spaced therefrom to form an annular gap accommodating the dependent skirt portion of the plunger.

10. The apparatus according to claim 9, wherein the external collar is rotatable with respect to the plunger, wherein locking structures allow axial movement of the plunger with respect to the frame at a given angular orientation.

11. The apparatus according to claim 10, wherein the locking structures include a visible indication of the angular orientation at which the plunger can be axially moved.

12. The apparatus according to claim 1, the frame further having an upstanding holding structure comprising at least one hole, wherein the mechanism configured to release the releasable striker lock when the plunger reaches the firing position comprises at least one cam surface configured to unhook a barb from the at least one hole.

13. The apparatus according to claim 1, wherein the releasable striker lock locks the striker to the frame to prevent axial movement of the striker.

* * * * *